(12) United States Patent
Gavrilova et al.

(10) Patent No.: US 8,318,485 B2
(45) Date of Patent: Nov. 27, 2012

(54) STEM CELL THERAPY FOR THE TREATMENT OF DIABETIC RETINOPATHY AND DIABETIC OPTIC NEUROPATHY

(76) Inventors: Natalie Gavrilova, Moscow (RU); Irina Saburina, Moscow (RU); Nikolay Mironov, Moscow (RU)

( * ) Notice: Subject to any disclaimer, the term of this patent is extended or adjusted under 35 U.S.C. 154(b) by 1055 days.

(21) Appl. No.: 12/036,424

(22) Filed: Feb. 25, 2008

(65) Prior Publication Data
US 2009/0214485 A1    Aug. 27, 2009

(51) Int. Cl.
| | |
|---|---|
| *C12N 5/07* | (2010.01) |
| *C12N 5/073* | (2010.01) |
| *C12N 5/074* | (2010.01) |
| *C12N 5/077* | (2010.01) |
| *C12N 5/0789* | (2010.01) |
| *C12N 5/079* | (2010.01) |
| *C12N 5/0797* | (2010.01) |

(52) U.S. Cl. ........ 435/368; 424/93.7; 435/366; 435/377
(58) Field of Classification Search .......................... None
See application file for complete search history.

(56) References Cited

U.S. PATENT DOCUMENTS

| | | |
|---|---|---|
| 2004/0219136 A1 | 11/2004 | Hariri |
| 2005/0031599 A1 | 2/2005 | Kooy et al. |
| 2005/0037491 A1 | 2/2005 | Mistry |
| 2005/0084963 A1 | 4/2005 | Chan-Ling |
| 2005/0129665 A1 | 6/2005 | Friedlander et al. |
| 2005/0148071 A1 | 7/2005 | Weiss |
| 2005/0176141 A1 | 8/2005 | Vanguri |
| 2005/0226852 A1 | 10/2005 | Toda |
| 2005/0244964 A1 | 11/2005 | Davidson |
| 2005/0282276 A1 | 12/2005 | Honmou et al. |
| 2005/0287665 A1 | 12/2005 | Cheng et al. |
| 2006/0104960 A1 | 5/2006 | Kooy et al. |

FOREIGN PATENT DOCUMENTS
WO    WO 2006/133052 A2    12/2006

OTHER PUBLICATIONS

Sengupta et al., Investigative Opthalmology and Visual Science, 46(1): 343-348, Jan. 2005.*
Torquetti et al. , Arq. Bras. Oftalmol. vol. 70, n.2, pp. 371-375, published online Nov. 2006.*
Klassen et al., Progress in Retinal and Eye Research, 23:149-181, 2004.*
Romanov et al., Stem Cells, 21:105-110, 2003.*

* cited by examiner

*Primary Examiner* — Daniel E Kolker
*Assistant Examiner* — Stacey N MacFarlane
(74) *Attorney, Agent, or Firm* — Timothy M. Brown

(57) ABSTRACT

The invention comprises methods and stem cell compositions for the treatment of diabetic retinopathy and other degenerative diseases of the eye. The invention is practiced in two stages with the first stage comprising the administration of neural stem cells to the eye, and the second stage comprising the administration of mesenchymal cells intravenously.

12 Claims, 32 Drawing Sheets

Fig. 14

| | Blood vessel index | FAG-Ophtalmoscopy | Doppler spectroscopy | ERG Amplitudes | | EOG | | Computer Perimetry | |
|---|---|---|---|---|---|---|---|---|---|
| | | | | red light waves | white light waves | OS | OD | OS | OD |
| Before | 10 | Signs of central chorioretinal dystrophy | Asymmetry of blood flow. Linear blood flow in eye artery and central retina artery is lower in OS. | a-,b- Dicreased in OD and OS | b-wave Increased in OD and OS | | AC is lower | Single absolute and relative scotomas | |
| Intravenous Treatment with MSC – Patient 1 | | | | | | | | | |
| 2 days (small edema is found) | | | | a-,b-waves are lowered in OD and OS | b-wave is lowered to normal | AC is increased | AC is increased greater than in OS. | Slight increase of ischemic processes level | |
| 6 days | | | | a-wave is increased 2 times for OD and 3.5 times for OS b-wave is increased 1.3 times for OD and 1.5 times for OS | b-wave is lowered 1.3 times to normal values for OD and OS | | AC is lower and close to normal values | | |
| 1 month | Index is lower | | | a-wave is higher than initially (high activity of retina central zone) | b-wave is close to the upper limit (reduction of ischemic processes) | AC is at the level close to normal | | Level of foveolar sensitivity is increased. Scotomas disappeared. | Number of scotomas is reduced to 4 absolute and 1 relative scotomas. |
| 2 months | | | | | | AC is at subnormal level | | | |
| 3 months (results are the same) | | | | | | | | | |

Fig. 15

| | Blood vessel index | FAG-ophthalmos copy | Doppler spectroscopy | ERG-Amplitudes | | EOG | | Computer Perimetry | | OCT |
|---|---|---|---|---|---|---|---|---|---|---|
| | | | | Red a-,b- waves | White a-,b- waves | OS | OD | OS | OD | |
| Before | 9 – subclinical stage of DR | Confirmed | Asymmetry of blood flow: OS – slightly abnormal OD – blood flow in eye and central retina artery increased twofold. | b- wave lower in OS, OD (hypoxia, ischemia) | b- wave lower in OS, OD (hypoxia, ischemia) | Super-normal (ischemia compensation) | Super-normal (ischemia compensation) | Normal | Normal | Thickness of optic nerve is less than normal in OS |
| Intravenous Treatment with MSC and NPC Retrobulbarly – Patient 2 | | | | | | | | | | |
| 2 days | | | Symmetry, lowering blood flow to normal | b-wave, slightly increase in OS, OD | | Lowering to subnormal | Lowering to subnormal | | | |
| 7 days | | | | | b- wave slightly increased in OD | | | | | |
| 45 days – no significant changes | | | | | | | | | | |
| 60 days | Index - lower | | | | | | | | | Thickness of optic nerve increased in OS, OD |

Fig. 16

| | Blood vessel index | FAG-ophtalmoscopy OS | FAG-ophtalmoscopy OD | Doppler spectroscopy | ERG-Amplitudes Red a-,b-waves | ERG-Amplitudes White a-,b-waves | EOG OS | EOG OD | Computer Perimetry OS | Computer Perimetry OD | OCT |
|---|---|---|---|---|---|---|---|---|---|---|---|
| Before treatment | 24 (severe changes) | numerous hemorthages exeudate | proliferative tissue of optic nerve in macular region, several hemorrhages, after laser coagulation | Slight reduction of blood flow in eye vessels | Significantly reduced all amplitudes (Pathological changes in outer layer of retina, lower activity of bipolar and Muller cells, both in the periphery and central zone) | | Reduced activity of pigment epithelium in both eyes, but in greater extent in OD | | Reduced foveolar sensitivity, in greater extent in OD than in OS. OS – absolute and relative scotomas. OD – relative scotomas. | | Significant reduction of optic nerve thickness in OS. OD: 99 μm. OS:59.9 μm. Lability of the nerve is reduced in OS, OD |
| Intravenous Treatment with MSC and NPC Retrobulbarly – Patient 3 ||||||||||||
| 2 days | | | | | a-,b- waves in red and white light increased in OS; b-wave in white and a-wave in red in OD is increased | | AC is increased (activity pigment epithelium increased) | | Significant increased the level of foveolar sensitivity in OD. | | |
| 7 days | | | | Blood flow is increased. | a-,b-waves of white light is higher than after 2 days | | Activity of pigment epithelium is reduced. AC in OS reduced to before treatment level. | | Reduction in number of absolute scotomas. Foveolar activity remains the same as after 2 days. | | |
| 14 days – no changes | | | | | | | | | | | |
| 30 days | 21 | | | | | | AC is reduced below initial. | | | | Thickness of optic nerve increased from 59.9 to 72.41 μm. Lability of nerve is increased. |
| 60 days | | Positive dynamics of disappearance of hemorrhages and absence of new ones. | | Blood flow is increased twice. | b-wave is greater than initial in OS. a-wave in OD, OS as initial, b-wave in OD as initially | a-,b- waves is greater than initial in OD | | AC is lower than initially | Foveolar activity remains the same as after 2 days | | |

Fig. 17

| | Blood vessel index | FAG-ophtal moscopy | Doppler spectroscopy | | ERG-Amplitudes | | EOG | | Computer Perimetry | | OCT |
|---|---|---|---|---|---|---|---|---|---|---|---|
| | | | OS | OD | Red a-,b- waves | White a-,b- waves | OS | OD | OS | OD | |
| Before Treatment Coagulation test showed increased level of fibrinogen and decrease thrombin time formation - super-coagulation | 14 (medium range) | Numerous hemorrhages, excudate | Blood flow is 5 times higher than in OD. | Strong asymmetry. | a-,b- waves are lower in OS and OD | b-wave is lower in OS and OD | Significant reduction of functional activity of pigment epithelium in OD and OS | | | | Cyst edema in ML in OD. |
| Intravenous Treatment with MSC and NPC Retrobulbarly – Patient 4 | | | | | | | | | | | |
| 2 days | | | Slight reduction of blood flow in OS. | | a-wave is increased to the normal in OD and OS | a-,b-wave are slightly increased | AC is increased in both eyes, and in OD is greater than in OS | | Tendency to increase of foveolar acrivity. | | |
| 7 days | | | Blood flow is normalized | Blood flow is greater but still lower than in norm. | | | Increase of pigment functional activity, no asymmetry. | Slight lowering of pigment functional activity. | | | |
| 14 days Fibrinogen level becomes lower tested on system level | | | Blood flow is normalized | OD: Slight increase of blood flow. | | | Increase of pigment functional activity to normal | Further lowering pigment functional activity | | | |
| 30 days Further decrease level of fibrinogen | 11 | Resorption of hemorrhages, no new micro bleedings appeared. | | | a-,b- waves is higher (1.5-2 times) in OD compared to initial OS: retina functional activity is increased | a-,b- waves is higher (1.5-2 times) in OD compared to initial | AC is lower but still higher than initially | | | Appearance of scotomas in central zone (possibly due to hypoxia because of small macular edema). | |

Fig. 18

| Type of differentiating | Medium components | Time of observation | Visual result |
|---|---|---|---|
| Adipose geneses | 0.5 mcM hydrocortisone 0.5 mcM Isobuthilcxantin 50mcM indomethacin | 21 days | Formation of lipid particles in cell cytoplasm |
| Osteogeneses | $10^{-8}$ M Dexamethazone 0.2mM Ascorbic acid 10mM glycerophosphate | 21 days | Formation of foci of mineralization |
| Chondrogeneses | 500ng/ml BmP-6 10ng dexamethazone 0.2mM ascorbic acid 10mM glycerophosphate | 21 days | Formation of suspended spheroids |
| Miogeneses | ITS 10-8 dexamethazone | 21 days | Promiotubes with central nuclear position |

Fig. 20 Patient 1: MSC treatment

Patient 3: MSC+NPC treatment

Improvement of blood flow in left and right eye after SC treatment
(Doppler spectroscopy)

Fig. 2L Patient 3: MSC+NPC treatment

Fig. 27 Patient 4: MSC+NPC treatment

Patient 5: MSC+NPC treatment

Fig. 30  Patient 5: MSC+NPC treatment

Before    1 month

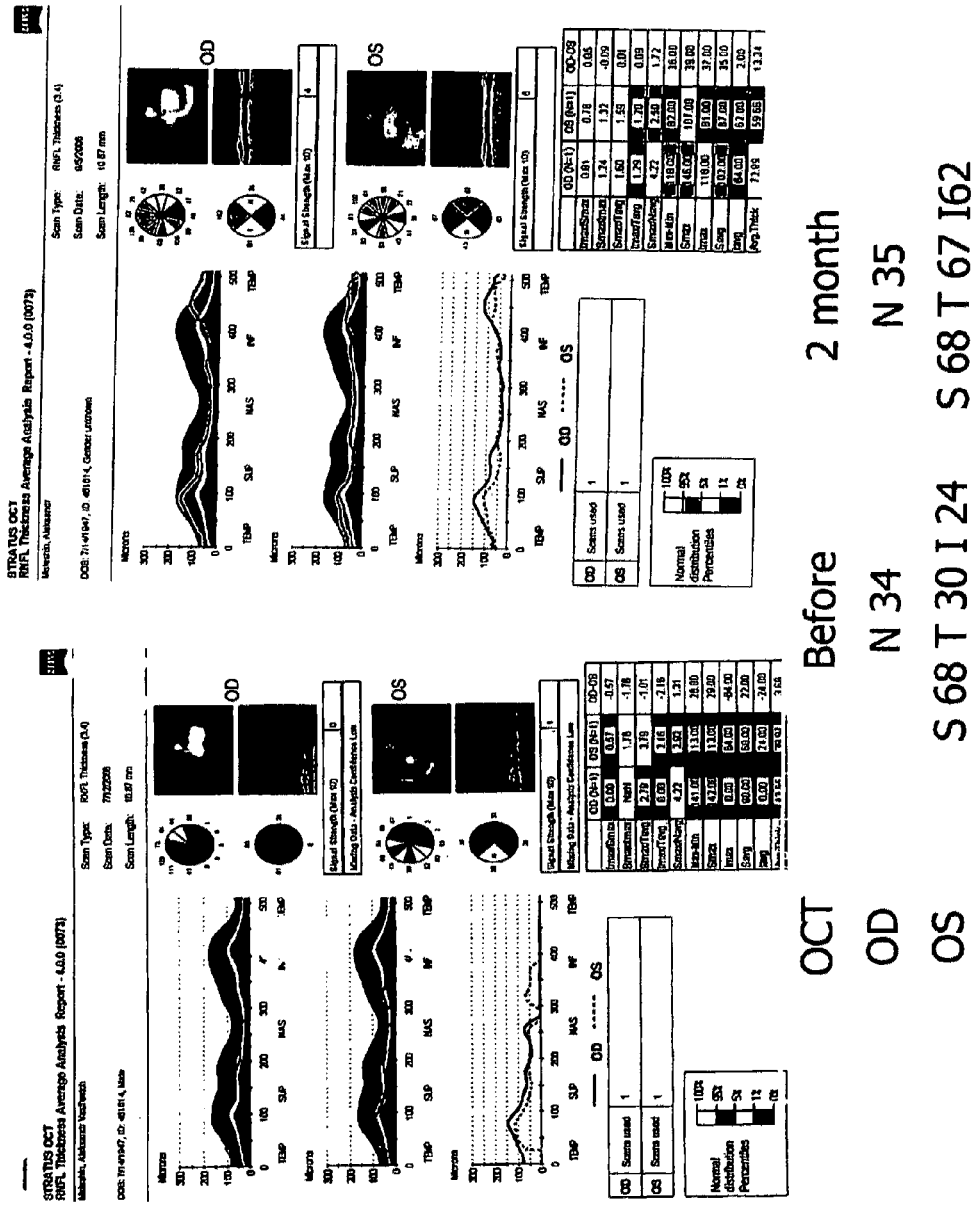
Fig. 35  Patient 7: MSC+NPC treatment

STEM CELL THERAPY FOR THE TREATMENT OF DIABETIC RETINOPATHY AND DIABETIC OPTIC NEUROPATHY

FIELD OF THE INVENTION

The present invention relates to cell-based therapy for ocular diseases and disorders. In particular, the invention provides pharmaceutical compositions, devices and methods for the regeneration or repair of cells and tissues of the retina using mesenchymal and ectodermal stem cells. More particularly, the invention concerns the treatment of diabetic retinopathy and diabetic optic neuropathy through the retinal administration of neural stem cells, and the intravenous administration of mesenchymal cells.

BACKGROUND OF THE INVENTION

The patents and publications referred to throughout the specification are incorporated herein by reference as if set forth verbatim.

The retina contains seven layers of alternating cells and processes that convert a light signal into a neural signal. The retinal photoreceptors and adjacent retinal pigment epithelium (RPE) form a functional unit that, in many disorders, becomes unbalanced due to genetic mutations or environmental conditions (including age). This results in loss of photoreceptors through apoptosis or secondary degeneration, which leads to progressive deterioration of vision and, in some instances, to blindness (for a review, see, e.g., Lund, R. D. et al. 2001, Progress in Retinal and Eye Research 20: 415-449). Two classes of ocular disorders that fall into this pattern are retinitis pigmentosa (RP) and age-related macular degeneration (AMD).

RP is mainly considered an inherited disease—over 100 mutations have been associated with photoreceptor loss (see Lund et al., 2001, supra). Though the majority of mutations target photoreceptors, some affect RPE cells directly. Together, these mutations affect such processes as molecular trafficking between photoreceptors and RPE cells and phototransduction, for example.

The primary disorder in AMD appears to be due to RPE dysfunction and changes in Bruch's membranes, e.g., lipid deposition, protein cross-linking and decreased permeability to nutrients (see Lund et al., 2001 supra). A variety of elements may contribute to macular degeneration, including genetic makeup, age, nutrition, smoking and exposure to sunlight.

Diabetic retinopathy, the leading cause of blindness in adults, results from abnormal circulation in the retina (National Eye Institute Website, www.nei.nih.gov; accessed Oct. 7, 2006). It begins with microaneurysms in the retina as areas of balloon-like swelling in the retina's tiny blood vessels are formed. These blood vessels become blocked depriving portions of the retina of a blood supply. This trauma causes the retina to secrete vascularization signals which result in new, abnormal blood vessels being formed. During this stage, known as proliferative diabetic retinopathy, the abnormal vessels proliferate along the retina and extend to the surface of the vitreous gel that fills the eye. The thin fragile walls of the abnormal vessels eventually leak blood into the vitreous gel causing vision loss and ultimately blindness. In the later phases of the disease, continued abnormal vessel growth and scar tissue may lead to further retinal degeneration including retinal detachment and glaucoma.

The two main treatments for diabetic retinopathy are photocoagulation and vitrectomy. Photocoagulation is a laser treatment that is used to treat advanced diabetic retinopathy (i.e. proliferative diabetic retinopathy). It involves the laser cauterization of the abnormal blood vessels that leak blood and other fluids into the vitreous gel of the eye. If there is a small amount of leakage, the laser is applied directly to specific points where the leaks occur (focal laser treatment). If the leakage is widespread or diffuse, laser burns are applied in a grid pattern over a broad area (grid laser treatment).

Panretinal photocoagulation is another laser-based treatment for diabetic retinopathy. According to this method, the entire retina (excluding the macula) is treated with scattered laser burns. This process causes the abnormal blood vessels to shrink thereby reducing the chances of hemorrhages in the vitreous gel.

Vitreoctomy provides another mode of treatment for diabetic retinopathy. A vitrectomy is a surgical procedure for correcting large blood vessel leaks in the vitreous gel. According to this procedure, the blood-filled vitreous is surgically removed from the eye. This hemorrhagic tissue is then replaced with a balanced salt solution to maintain the eye's shape and interocular pressure.

Photocoagulation and vitrectomies only offer a temporary solution to the vision loss caused by diabetic retinopathy. This is because these procedures only treat abnormal blood vessel formation as it occurs. They do not offer a lasting solution that addresses the cause of abnormal blood vessel formation which is compromised retinal circulation. As a result, photocoagulation and vitrectomies must be performed repeatedly in order to maintain long-term vision. Panretinal photocoagulation also has the undesirable side effect of causing the loss of peripheral vision and compromised night vision. A drawback of vitrectomy is that it requires a long recovery period during which the patient must remain facing the ground.

What is needed is a diabetic retinopathy treatment that prevents the abnormal blood vessel formation that leads to lost vision.

SUMMARY OF THE INVENTION

The present invention provides compositions and methods applicable to cell-based or regenerative therapy for retinal diseases and disorders. In particular, the invention features pharmaceutical compositions, devices and methods for the regeneration or repair of retinal tissue using mesenchymal and ectodermal stem cells.

One aspect of the invention is a method for treating a retinal disorder comprising administering to an individual in need thereof an ectodermal stem cell population to the individual's retinal tissue, and intravenously administering to the individual a mesenchymal stem cell population. In a particular embodiment, the ectodermal stem cells are derived from fetal neural tissue. Another aspect of the invention concerns deriving the mesenchymal stem cell population from a source selected from at least one of umbilical cord blood, adult bone marrow and placenta. In still another aspect of the invention, the retinal disorder is one or more of macular degeneration, retinitis pigmentosa, diabetic retinopathy, glaucoma or limbal epithelial cell deficiency. In certain embodiments, the cells are induced in vitro to differentiate into a neural or epithelial lineage cells prior to administration. In certain embodiments, the cells are administered with at least one other agent, such as a drug for ocular therapy, or another beneficial adjunctive agent such as an anti-inflammatory agent, anti-apoptotic agents, antioxidants or growth factors. In these embodiments, the other agent can be administered simultaneously with, or before, or after, the postpartum cells.

According to another aspect of the invention, a method is provided for treating a patient having a retinal disorder, which comprises administering to the patient at least one preparation selected from a cell lysate of ectodermal cells, a cell lysate of mesenchymal cells, media conditioned by ectodermal cells, and media conditioned by mesenchymal cells. In one aspect of the invention, the ectodermal cells are derived from fetal neural tissue. In another aspect of the invention, the mesenchymal cells are derived from at least one of umbilical cord blood, bone marrow and placenta.

Also featured in accordance with the present invention is a cell lysate prepared from mesenchymal stem cells and/or ectodermal stem cells. The cell lysate, may be separated into a membrane enriched fraction and a soluble cell fraction. The invention also features an extracellular matrix produced by the postpartum-derived cells, as well as a conditioned medium in which the cells have been grown.

According to yet another aspect of the invention, a kit is provided for treating a patient having an retinal degenerative condition. The kit comprises a pharmaceutically acceptable carrier comprising a population of multipotent mesenchymal stem cells (MMSCs), and a pharmaceutically acceptable carrier comprising ectodermal cells, and instructions for administering said MMSCs and said ectodermal cells in the treatment of a retinal degenerative condition. The multipotent mesenchymal stem cells may be derived from umbilical cord blood, placenta, Wharton's jelly, bone marrow, chorionic villus, adipose tissue, menstrual discharge, amniotic fluid and peripheral blood, or combinations thereof. In some embodiments, the ectodermal cells for use in the inventive kit are derived from fetal neural tissue. The kit instructions may be printed on a printable medium, presented using an electronic format such as a CD-ROM or similar electronic storage means, as well as combinations thereof. The kit may optionally contain one or more additional components, such as reagents and, instructions for culturing the cells, or a population of at least one other cell type, or one or more agents useful in the treatment of an ocular degenerative condition. In one particular embodiment, the multipotent or pluripotent cells are isolated from umbilical cord blood. In another particular embodiment, the ectodermal cells are derived from fetal neural tissue.

Other features and advantages of the invention will be apparent from the detailed description and examples that follow.

BRIEF DESCRIPTION OF THE DRAWINGS

FIG. 14 shows a table of the pre- and post-operative results for Patient 1 after intravenous injection of mesenchymal cells.

FIGS. 15-17 show the pre- and post-operative results for Patients 2-4 after the intravenous injection of mesenchymal cells and the retrobulbar injection of neural progenitor cells.

FIG. 18 is a table showing the results of the in vitro differentiation of bone marrow stem cells from Example 3.

FIGS. 22-35 show the pre- and post-operative results for Patients 2-7 after the intravenous injection of mesenchymal cells and the retrobulbar injection of neural progenitor cells.

DEFINITIONS

Figure 1:
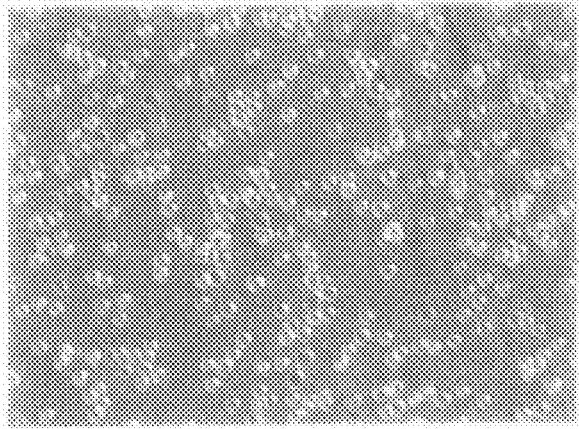
FIG. 1 shows, a phase-contrast microscopy (PCM) image of a primary suspension of dissociated brain tissue cells from an embryo at 10 weeks of development.

Stem cells are undifferentiated cells defined by the ability of a single cell both to self-renew, and to differentiate to produce progeny cells, including self-renewing progenitors, non-renewing progenitors, and terminally differentiated cells. Stem cells are also characterized by their ability to differentiate in vitro into functional cells of various cell lineages. Stem cells may have varying degrees of potency. Pluripotent stem cells are capable of giving rise to cells belonging to each of the three embryonic germ layers (i.e. the endoderm, mesoderm and ectoderm). Multipotent stem cells are more lineage restricted than pluripotent stem cells as they are only capable of forming cells from a single lineage (e.g. ectodermal cells). Stem cells may also be progenitor cells (i.e. precursor cells) which are lineage-committed cells capable of both dividing and differentiating into a specific terminal cell type. Fetal neural stem cells are derived from the neural tissue of a mammalian fetus after at least 7 to 12 weeks of gestation. In the case of humans, fetal neural stem cells are typically but not isolated exclusively between 7 and 12 weeks of gestation.

"Multipotent," or "multipotency," refers to the ability of a stem cell to differentiate into various cells of one embryonic germ layer lineage (i.e the ectoderm, endoderm or mesoderm).

"Pluripotent," or "pluripotency," refers to the ability of a stem cell to differentiate into the various cells from each of the three embryonic germ layer lineages (i.e the ectoderm, endoderm and mesoderm).

Stem cells are also categorized on the basis of their source. An adult stem cell is generally a multipotent undifferentiated cell found in tissue comprising multiple differentiated cell types. The adult stem cell can renew itself. Under normal circumstances, it can also differentiate to yield the specialized cell types of the tissue from which it originated, and possibly other tissue types. An embryonic stem cell is a pluripotent cell from the inner cell mass of a blastocyst-stage embryo. A fetal stem cell is one that, originates from fetal tissues or membranes. A postpartum stem cell is a multipotent or pluripotent cell that originates substantially from extraembryonic tissue available after birth, namely, the placenta and the umbilical cord. These cells have been found to possess features characteristic of pluripotent stem cells, including rapid proliferation and the potential for differentiation into many cell lineages. Postpartum, stem cells may be blood-derived (e.g., as are those obtained from umbilical cord blood) or non-blood-derived (e.g., as obtained from the non-blood tissues of the umbilical cord and placenta).

The terms "precursor cell," "tissue precursor cell" and "progenitor cell" are used interchangeably herein and refer to a lineage-committed cell that divides and differentiates to form new, specialized tissue(s). Endothelial precursor cells are one example of a precursor cell. It should be understood that an "endothelial progenitor cell" is used interchangeably with the term "endothelial precursor cell" to denote regenerative cells capable of forming endothelial tissues.

Embryonic tissue is typically defined as tissue originating from the embryo (which in humans refers to the period from fertilization to about six weeks of development. Fetal tissue refers to tissue originating from the fetus, which in humans refers to the period from about six weeks of development to parturition. Extraembryonic tissue is tissue associated with, but not originating from, the embryo or fetus. Extraembryonic tissues include extraembryonic membranes (chorion, amnion, yolk sac and allantois), umbilical cord and placenta (which itself forms from the chorion and the maternal decidua basalis). Differentiation is the process, by which an unspecialized ("uncommitted") or less specialized cell acquires the features of a specialized cell, such as a nerve cell or a muscle cell, for example. A differentiated cell is one that has taken on a more specialized ("committed") position within the lineage of a cell. The term committed, when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. Dedifferentiation refers to the process by which a cell reverts to a less specialized (or committed) position within the lineage of a cell. As used herein, the lineage of a cell defines the heredity of the cell, i.e. which cells it came from and what cells it can give rise to The lineage of a cell places the cell within a hereditary scheme of development and differentiation.

"Regenerative" is used to refer to the ability of a substance to restore, supplement or otherwise rehabilitate the natural function of a tissue. This ability may be conferred by, for example, treating a dysfunctional tissue with regenerative cells. Regenerative cells treat dysfunctional tissue by replacing it with new cells capable of performing the tissue's natural function, or by helping to restore the natural activity of the dysfunctional tissue.

The terms "restore," "restoration" and "correct" are used interchangeably herein and refer to the regrowth, augmentation, supplementation, and/or replacement of a defective tissue with a new and preferentially functional tissue. The terms include the complete and partial restoration of a defective tissue. Defective tissue is completely replaced if it is no longer present following the administration of the inventive composition. Partial restoration exists where defective tissue remains after the inventive composition is administered.

The phrase "effective amount" refers to a concentration or amount of a reagent or pharmaceutical composition, such as a growth factor, differentiation agent, trophic factor, cell population or other agent, that is effective for producing an intended result, including cell growth and/or differentiation in vitro or in vivo, or treatment of ocular degenerative conditions, as described herein. With respect to the administration of one or more populations of regenerative cells as disclosed herein, an effective amount may range from as few as several hundred or fewer to as many as several million or more. It will be appreciated that the number of cells to be administered will vary depending on the specifics of the disorder to be treated, including but not limited to size or total volume/surface area to be treated, as well as proximity of the site of administration to the location of the region to be treated, among other factors familiar to the medicinal biologist.

A "clone," or "clonal cell," is a line of cells that is genetically identical to the originating cell. This cloned line is produced by cell division (mitosis) of the originating cell. The term "clonal population" in reference to the cells of the invention shall mean a population of cells that is derived from a clone. A cell line may be derived from a clone and is an example of a clonal population.

The term "cell line" refers to a population of cells cultured in vitro that has descended through one or more generations (and possibly cultures) from a single primary culture or a clone. The cells of a cell line share common characteristics.

"Mesenchymal cells" are mesodermal germ lineage cells which may or may not be differentiated. The mesenchymal cells of the invention include cells at all stages of differentiation beginning with multipotent mesodermal germ cells, down to fully differentiated terminal cells. Examples of mesenchymal cells which are terminal cells include, but are not limited to, endothelial cells, fibroblasts, osteoblasts, chondrocytes, myocytes, and adipocytes. The mesenchymal cells of the invention may be multipotent stem cells capable of forming multiple cells belonging to the mesodermal lineage (i.e. multipotent mesenchymal stromal cells or "MMSCs"). Mesenchymal cells may also be regenerative precursor cells capable of dividing and differentiating into a specific terminal cell. Endothelial precursor cells are one example of a mesenchymal cell. The mesenchymal cells of the invention may be derived from sources including umbilical cord blood, placenta, Wharton's jelly, bone marrow, chorionic villus, adipose tissue, menstrual discharge, amniotic fluid and peripheral blood, and combinations thereof. Mesenchymal cells may also be derived from the in vitro differentiation of pluripotent embryonic stem cells.

In a broad sense, a progenitor cell is a cell that has the capacity to create progeny that are more differentiated than itself, and yet retains the capacity to replenish the pool of progenitors. By that definition, stem cells themselves are also progenitor cells, as are the more immediate precursors to terminally differentiated cells. When referring to the cells of the present invention, as described in greater detail below, this broad definition of progenitor cell may be used. In a narrower sense, a progenitor cell is often defined as a cell that is intermediate in the differentiation pathway, i.e., it arises from a stem cell and is intermediate in the production of a mature cell type or subset of cell types. This type of progenitor cell is generally not able to self-renew. Accordingly, if this type of cell is referred to herein, it will be referred to as a non-renewing progenitor cell or as an intermediate progenitor or precursor cell.

As used herein, the phrase "differentiates into an ocular lineage or phenotype" refers to a cell that becomes partially or fully committed to a specific ocular phenotype, including without limitation, retinal and corneal stem cells, pigment epithelial cells of the retina and iris, photoreceptors, retinal ganglia and other optic neural lineages (e.g., retinal glia, microglia, astrocytes, Mueller cells), cells forming the crystalline lens, and epithelial cells of the sclera, cornea, limbus and conjunctiva. The phrase "differentiates into a neural lineage" or "phenotype" refers to a cell that becomes partially or fully committed to a specific neural phenotype of the CNS or PNS, i.e., a neuron or a glial cell, the latter category including without limitation astrocytes, oligodendrocytes, Schwann cells and microglia.

An ectodermal cell is any cell that belongs to the group of cells that develop from the ectoderm germ layer. The ectodermal cells of the invention have varying degrees of potency and varying levels of differentiation. Examples of ectodermal cells include, but are not limited to; (a) multipotent cells capable of forming any cell type that originates from the ectoderm germ layer cell; (b) lineage-committed progenitor cells capable of dividing to form more progenitor cells or lineage-committed cells which differentiate into specialized, terminal cells; and (c) fully differentiated terminal cells that have a specific phenotype that supports a tissue function (e.g. neural cells, glial cells and keratinocytes). The ectodermal cells of the invention may be obtained by methods including, but not limited to, isolation from adult or prenatal tissue, expansion from a primary culture of ectodermal cells, or expansion from an ectodermal cell line.

The phrase "retinal disorder" is used to describe a defect in the tissue of the retina. Retinal disorders may result from infection, injury, or a degenerative condition. Degenerative conditions include, but are not limited to, macular degeneration, retinitis pigmentosa, diabetic retinopathy, glaucoma and limbal epithelial cell deficiency. The term retinal disorder includes any condition that leads to the impairment of the retina's normal function.

The term ocular degenerative condition (or disorder) is an inclusive term encompassing acute and chronic conditions, disorders or diseases of the eye, inclusive of the neural connection between the eye and the brain, involving cell damage, degeneration or loss. An ocular degenerative condition may be age-related, or it may result from injury or trauma, or it may be related to a specific disease or disorder. Acute ocular degenerative conditions include, but are not limited to, conditions associated with cell death or compromise affecting the eye including conditions arising from cerebrovascular insufficiency, focal or diffuse brain trauma, diffuse brain damage, infection or inflammatory conditions of the eye, retinal tearing or detachment, intra-ocular lesions (contusion penetration, compression, laceration) or other physical injury (e.g., physical or chemical burns). Chronic ocular degenerative conditions (including progressive conditions) include, but are not limited to, retinopathies and other retinal/macular disorders such as retinitis pigmentosa (RP), age-related macular degeneration (AMD), choroidal neovascular membrane (CNVM); retinopathies (i.e. retinal disorders) such as diabetic retinopathy, occlusive retinopathy, sickle cell retinopathy and hypertensive retinopathy, central retinal vein occlusion, stenosis of the carotid artery, optic neuropathies such as glaucoma and related syndromes; disorders of the lens and outer eye, e.g., limbal stem cell deficiency (LSCD), also referred to as limbal epithelial cell deficiency (LECD), such as occurs in chemical or thermal injury, Steven-Johnson syndrome, contact lens-induced keratopathy, ocular cicatricial pemphigoid, congenital diseases of aniridia or ectodermal dysplasia, and multiple endocrine deficiency-associated keratitis.

The phrase "treating an ocular degenerative condition" refers to ameliorating the effects of, or delaying, halting or reversing the progress of, or delaying or preventing the onset of, an ocular degenerative condition as defined herein.

The term "patient," or "subject," refers to animals, including mammals, preferably humans, who are treated with the pharmaceutical compositions or in accordance with the methods described herein.

The term "pharmaceutically acceptable carrier" (or medium), which may be used interchangeably with the term "biologically compatible carrier" (or medium), refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio.

Various terms are used to describe cells in culture. "Cell culture" refers generally to cells taken from a living organism and grown under controlled condition ("in culture" or "cultured"). A "primary cell culture" is a culture of cells, tissues, or organs taken directly from an organism(s) before the first subculture. Cells are expanded in culture when they are placed in a growth medium under conditions that facilitate cell growth and/or division, resulting in a larger population of the cells. When cells are expanded in culture, the rate of cell proliferation is sometimes measured by the amount of time needed for the cells to double in number. This is referred to as "doubling time."

The terms "ocular," "ophthalmic" and "optic" are used interchangeably herein to define "of, or about, or related to the eye."

A cell line is a population of cells formed by one or more subcultivations of a primary cell culture. Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but not limited to the seeding density, substrate, medium, growth conditions, and time between passaging.

The phrase "administering ectodermal cells" refers to the therapeutic introduction of ectodermal cells to a subject. Administration may take place by any route that allows the ectodermal cells to treat a retinal tissue disorder. The ectodermal cells may be directly administered to the eye of the patient through a variety of modes including, but not limited to, retrobulbar injection, intravitreous injection, and subchoroidal injection.

Several terms are used herein with respect to cell replacement therapy. The terms autologous transfer, autologous transplantation, autograft and the like refer to treatments wherein the cell donor is also the recipient of the cell replacement therapy. The terms allogeneic transfer, allogeneic transplantation, allograft and the like refer to treatments wherein the cell donor is of the same species as the recipient of the cell replacements therapy, but is not the same individual. A cell transfer in which the donor's cells and have been histocompatibly matched with a recipient is sometimes referred to as a syngeneic transfer. The terms xenogeneic transfer, xenogeneic transplantation, xenograft and the like refer to treatments wherein the cell donor is of a different species than the recipient of the cell replacement therapy.

"Retinal tissue" refers to the neural cells and associated vasculature that line the back of the eye. Structures within retinal tissue include the macula and fovea. Retinal tissue further includes the tissue that is juxtaposed to these neural cells (e.g. pigment epithelia) and associated vasculature.

DETAILED DESCRIPTION

The invention relates to methods and compositions for treating ocular disorders. In particular, the invention relates to the administration of ectodermal and mesenchymal cells in the treatment of retinal disorders. More particularly, the invention concerns treating diabetic retinopathy by administering neural stem cells to the retina, and intravenously administering mesenchymal cells.

The ectodermal cells of the invention are retinal-regenerative cells in the sense that they replace defective retinal tissue and/or restore the normal function of the retina. Thus, the etodermal cells have the ability to form neural tissue or enhance neural tissue function. Cells having this property may be derived from a variety of sources.

In one embodiment of the invention, a retinal disorder is treated using ectodermal stem cells derived from prenatal tissue. One source of prenatal ectodermal stem cells is the ectodermal embryonic germ layer. Embryonic ectodermal cells suitable for treating retinal disorders, and their methods of isolation, are known in the art.

In another embodiment of the invention, prenatal ectodermal cells are stem cells derived from fetal neural tissue. Fetal neural tissues suitable for providing retinal-regenerative cells include, but are not limited to, the telencephalon, diencephalon, forebrain, midbrain, cerebellum, pons and medulla, and spinal cord. Treating retinal disorders with combinations of cells derived from these tissues are also within the scope of the invention.

Examples of fetal neural stem cells capable of treating retinal disorders, and their methods of isolation include, but are not limited to: U.S. Pat. No. 6,852,532; U.S. Pat. App. 20020012903; U.S. Pat. App. No. 20020168767; Kallur et al. J Neurosci Res. 2006 October 16 (Epub ahead of print); Eriksson et al. Exp Neurol. 2003 December, 184(2):615-35; Espinosa-Jeffrey J Neurosci Res. 2002 Sep. 15; 69(6):810-25; Kim et al. Exp Neurol. 2006 May; 199(i):222-35. Epub 2006 May 22; Englund et al. Exp Neurol. 2002 January; 173(1):1-21; Belicchi et al. J Neurosci Res. 2004 Aug. 15; 77(4):475-86; and Svendsen et al. Exp Neurol. 1997 November; 148(1): 135-46. Fetal neural stem cells suitable for practicing the invention may be allogeneic or xenogeneic in nature. Neural stem cells for use with the invention need not be derived from a primary culture of mammalian neural tissue. Thus, it is also contemplated that retinal disorders, such as diabetic retinopathy, for example, may also be treated with neural stem cells which are expanded from a clonal cell line. One cell line suitable for practicing the methods disclosed herein are taught in Flax et al. (Nat. Biotechnol. 1998 November; 16(11):1033-9), the disclosure of which is incorporated herein by reference.

The ectodermal cells of the invention may be delivered to retinal tissue through a variety of routes. In general, any administration route that places the ectodermal cells in contact with the retinal tissue may be used. In one embodiment of the invention, the ectodermal cells are injected intraocularly. Suitable intraocular injection routes, include, but are not limited to, retrobulbarly, subconjuctivally, intravitreally, suprachoroidally, and subretinally. These routes may be used singularly, or in combination.

It is also contemplated that the ectodermal cells of the invention may be administered through other routes including systemically (e.g. intravenous injection), topically, and/or periocularly. These routes may be used alone or in combination with the intraocular routes of administration discussed above.

Another aspect of the invention relates to the intravenous administration of mesenchymal cells. Like their ectodermal counterpart, the mesenchymal cells of the invention may differ in their level of potency and degree of specialization. Thus, mesenchymal cell potency can range from multipotent mesenchymal stem cells that can form all cells of the mesoderm lineage, down to fully differentiated terminal cells including, but not limited to, endothelial cells, fibroblasts, osteocytes, myocytes and chondrocytes.

Another aspect of the invention relates to the timing of the administration of the ectodermal and mesenchymal cells. An embodiment of the method involves simultaneously administering ectodermal cells to the retinal tissue and intravenously administering mesenchymal cells. In other useful embodiments, the cells are administered within 48 hours of each other.

Multipotent mesenchymal cells for treating ocular disorders (e.g. retinal disorders and specifically, diabetic retinopathy) may be derived from a variety of sources. In one aspect of the invention, multipotent mesenchymal cells are derived from embryonic mesoderm tissue. In another aspect of the invention, multipotent mesenchymal cells are derived from adult tissues, including, but not limited to bone marrow, peripheral blood and adipose tissue. It is also within the scope of the invention to isolate multipotent mesenchymal stem cells from tissues such as umbilical cord blood and placenta.

The mesenchymal cells of the invention may be derived from a variety of tissues. As noted above, mesenchymal cells can be isolated from embryonic tissues, fetal tissues, neonatal tissues, adult tissues and combinations thereof. It is also within the scope of the invention to derive mesenchymal cells from at least one of fetal cord blood and placenta. The specific tissues that provide a sufficient source of adults mesenchymal cells includes, but is not limited to bone marrow, blood, muscle, skin and adipose tissue.

Mesenchymal cells for treating retinal disorders and other ocular dysfunctions may be derived from human and non-human sources. Thus, the mesenchymal cells of the invention may be syngeneic, allogeneic or xenogeneic in nature.

Mesenchymal stem cells for practicing the invention may be isolated using any suitable technique that produces viable cells capable performing the functions and methods set out in the present disclosure. The isolation and culture of mesenchymal cells is a highly developed art that has been in practice for many years (see e.g. Werb et al. (11974) J. Biochem. 137, 373-385). Thus, methods for isolating mesenchymal stem cells are readily available in the art. Examples of these methods include, but are not limited to, the following references which are incorporated by reference: U.S. Pat. No. 5,486,359; U.S. Pat. No. 6,039,760; U.S. Pat. No. 6,471,958; U.S. Pat. No. 5,197,985; U.S. Pat. No. 5,226,914; WO92/22584; U.S. Pat. No. 5,827,735; U.S. Pat. No. 5,811,094; U.S. Pat. No. 5,736,396; U.S. Pat. No. 5,837,539; U.S. Pat. No. 5,837,670; U.S. Pat. No. 5,827,740; Jaiswal, N., et al., J. Cell Biochem. (1997) 64(2): 295 312; Cassiede P., et al., J. Bone Miner. Res. (1996) 11(9): 1264 1273; Johnstone, B., et al., (1998) 238(1): 265 272; Yoo, et al., J. Bone Joint Sure. Am. (1998) 80(12): 1745 1757; Gronthos, S., Blood (1994) 84(12): 41644173; and Makino, S., et al., J. Clin. Invest. (1999) 103(5): 697 705). Cell surface markers provide another means for isolating mesenchymal cells. Epitopes on the surface of the human mesenchymal stem cells are reactive with certain monoclonal antibodies known as SH2, SH3 and SH4 described in U.S. Pat. No. 5,486,359. These antibodies can be used as reagents to screen and capture a mesenchymal stem cell population from a heterogeneous cell population such as that found in the bone marrow.

Although in a preferred embodiment the mesenchymal stem cells are culturally expanded prior to use, it is also possible to use such mesenchymal stem cells without culture expansion. For example, mesenchymal stem cells may be derived from bone marrow and used after separation of blood cells therefrom, without expansion. Thus, for example, allogeneic bone marrow may be enriched in allogeneic human mesenchymal stem cells by removal of blood cells, and introduced into a patient.

Example 1

Preparation of Multipotent Mesenchymal Stromal Cells (MMSC) from Human Bone Marrow 1. Characteristics and Transport of the Donor Material The source for the preparation of human MMSC was a bone marrow suspension (BMS) obtained by puncture of the iliac crest.

The mandatory clinical, laboratory, and instrumental examinations of the patient (for autotransplantation) were performed, including:
 1. The filling out of the medical history with an attachment of copies of all discharges from the medical history during previous stages of treatment and examination
 2. Complete clinical blood tests
 3. Complete blood biochemistry panel, with determination of renin, aldosterone, and brain natriuretic peptide
 4. Blood group, Rhesus factor
 5. Blood test for HIV and Wasserman test
 6. Blood test for hepatitis B and C markers
 7. Complete immune status
 8. Chest x-ray
 9. Ultrasound of abdominal organs, kidneys
 10. ECG, Halter monitoring
 11. Electrocardiography (rest, exercise)
 12. Myocardial Scintigraphy
 13. Coronarography BMS was harvested from the posterior iliac crest. The material was harvested in, a procedures room with the necessary assortment of surgical and anesthesiology instruments. Exfusion of BMS was performed in accordance with approved methodology, Instructions for the Preparation of Autologous Bone Marrow from Patients for Clinical Use—Ministry of Health (Russia), No. 14/2 of 8 Jan. 1980, and procedural recommendations "Transplantation of Bone Marrow in Acute Radiation Disease in Humans"—Ministry of Health of 3 Nov. 1986.

After the skin was treated with iodine-containing solutions, in the area of the posterior crest, a puncture was made through the skin and subcutaneous fatty tissue, through which aspiration needles were inserted. After this, the cortical plate of the iliac crest was pierced and the bone marrow was aspirated from the spongy substance of the bone. To collect 20-50 mL of bone marrow, several punctures of the bone cortical plate were made. This required the skin and subcutaneous fatty tissue to be moved aside using the aspiration needle. (The classic technology requires the aspiration of bone marrow in small batches from each puncture (3-5 mL in a 20-mL syringe); nevertheless, the amount of BMS, extracted from each puncture, can reach 20-50 mL, if the bone marrow flow is good.) Following aspiration, the bone marrow preparation was transferred to a polymer container with anticoagulant.

After harvesting was completed a bandage was applied where the skin was punctured and the BMS was immediately sent to the laboratory for further processing. The amount of BMS collected was 20-100 mL.

The BMS was transported to the laboratory in a sterile polymer container containing anticoagulant (heparin). Transportation of the BMS was carried out with strict observance of aseptic and temperature conditions: the container with the bone marrow suspension was placed in a hermetically sealing isothermal container for transport (+2 to +4° C.). Transportation of the BMS should not exceed 2 hours.

The bone marrow suspension received by the laboratory was tested for infectious agents (by PCR or serological/bacteriological tests). The sample was found to be negative for: HIV-1 and -2; HPV-1 and II; HBV; HCV; CMV; HSV-1 and 2; *toxoplasma gondii, mycoplasma*; Epstein-Barr virus; *ureaplasma; Chlamydia; treponema pallidum*; enterococci; *candida* species; *aspergillus* species; *e. coli*; staphylococci; streptococci and *neisseria gonorrhoeae*.

The work with BMS in the laboratory is performed in accordance with the recommendations "Instructions for Controlling the Sterility of Stored Blood, Its Components, Preparations for Preserved Bone Marrow, Blood Substitutes, and Preservation Solutions"—Ministry of Health No. 4-42-4-85 of 17 Sep. 1985.

In accordance with technological regulations, the cell phenotype is monitored for specific, satellite, and negative markers at all stages of the cell transplant preparation, and the contamination test is performed in accordance with the approved cell culture certificate.

2. Preparation of Fractions of Nucleated Cells from Human Bone Marrow Suspension Plasma, extraneous material (bone fragments, fat), and erythrocytes were removed from the BMS aspirate.

2.1. An equal volume of PBS solution was added to the BMS aspirate.

2.2. The mixture was added over a Ficoll-Pague solution (Pharmacia) and centrifuged at 400 g for 30 minutes at 10° C.

2.3. The middle fraction of nucleated cells was collected, washed with PBS, and centrifuged at 200 g for 10 minutes.

2.4. The fraction was then resuspended in a hypotonic buffer solution for final elimination of erythrocytes and centrifuged. The hemolyzed supernatant was removed.

The obtained suspension of nucleated cells was plated in plastic dishes in growth medium DMEM/F12 (1/1) (Gibco, Grand Island), containing 20% fetal calf serum (HyClone, USA), 2 mM glutamine, and antibiotics. The plating density of the primary cell suspension was 500,000%1,000,000 cells/$cm^2$ on average. Cells were cultured under standard conditions (at 37° C. in an atmosphere of 5% $CO_2$). After a day, unattached cells were removed, and attached cells were incubated to 70-80% confluence, which generally takes from 10 to 20 days. The culture medium was replaced every 3 days.

Figure 8:
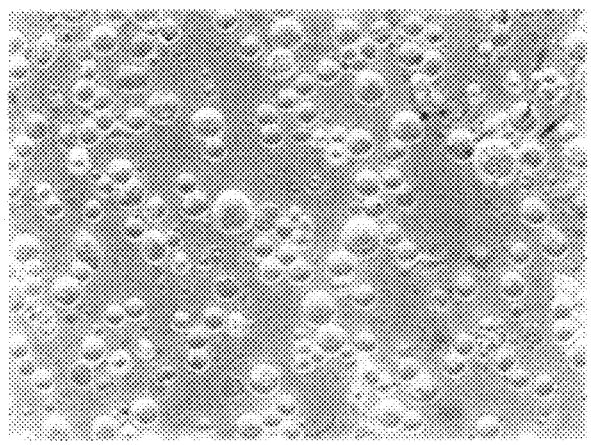
FIG. 8 is a microscopic image of a primary bone marrow cell suspension.
Figure 9:
FIGS. 9 and 10 depict microscopic images of primary human bone marrow cell cultures at 4 and 10 days respectively.
Figure 10:
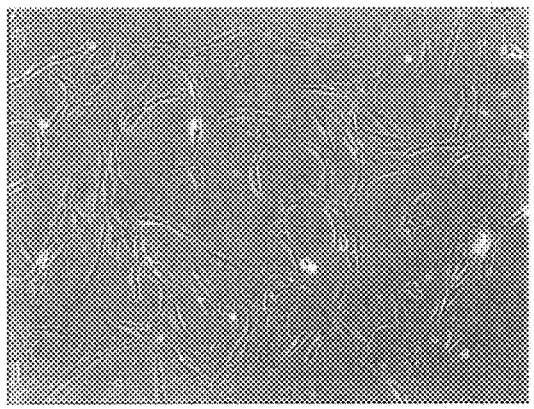

FIG. 8 is an image of the primary cell suspension obtained from the bone marrow aspirate, while FIGS. 9 and 10 depict the primary bone marrow cell culture at 4 and 10 days respectively.

After negative results on contamination were obtained, the material was transferred from the quarantine workstation to the culturing workstation.

3.3. Preparation of Cultures, Enriched with MMSC

To select stem populations, MMSC cultures are serially cloned at a low density.

- 3.1. For this purpose, the condensed medium was removed from petri dishes with the primary monolayer culture, reaching 80% confluence, using a 10-mL sterile plastic pipette.
- 3.2. The petri dishes were washed three times with Versene solution using a 10-mL pipette; then using a 5-mL sterile plastic pipette 2-3 mL of trypsin solution (0.25%) was added, and the dishes were incubated at 37° C., 5% $CO_2$ for 5-7 minutes.
- 3.3. The suspension obtained after incubation was homogenized using a 10-mL sterile plastic pipette or Pipetman with a 1-mL tip.
- 3.4. Up to 10 mL of growth medium was added to the suspension and this was pipetted with a 10-mL sterile plastic pipette until a homogeneous suspension was obtained.
- 3.5. The number of cells in the obtained suspension was counted using a Goryaev chamber.
- 3.6. The material was replated in new dishes at a density of 3-4 cells per 1 $cm^2$.
- 3.7. Up to 10 mL of growth medium was added to the petri dishes using a 10-mL sterile plastic pipette.
- 3.8. The medium was changed every 3 days.

Protocol for Replacing the Growth Medium (Once in 3 Days)

- 3.8.1. The condensed medium was removed from the petri dish with a 10-mL sterile plastic pipette.
- 3.8.2. The removed condensed medium was replaced with new medium using a 10-mL sterile plastic pipette in an amount corresponding to the petri dish volume (90 mm-9-10 mL of medium).
- 3.9. After 10-14 days of culturing with monitoring with an inverted microscope, homogeneous, dense colonies of small cells (7-10 µm in diameter) with a large number of mitoses were selected from dishes, first treated with 1 mM EDTA.
- 3.10. The colonies were cultured further at a density of 10-50 cells per $cm^2$ in the same growth medium at 37° C. in an atmosphere, containing 5% $CO_2$ and at 95%: humidity. The culture medium was replaced every 3 days.
- 3.11. To reach 50% confluence, the culture was plated at a plating density of 10-50 cells per $cm^2$. The number of culture passages did not exceed 5-7.

Protocol for Culture Passaging

- 3.11.1. The condensed medium was removed from petri dishes with the monolayer culture, reaching 50% confluence, using a 10-mL sterile plastic pipette.
- 3.11.2. 2-3 mL of trypsin solution was added to the petri dishes using a 5-mL sterile plastic pipette, and the dishes were incubated at 37° C., 5% $CO_2$ for 5-7 minutes.
- 3.11.3. The suspension obtained after incubation was homogenized using a 10-mL sterile plastic pipette.
- 3.11.4. Up to 10 µmL, of nutrient medium was added to the suspension and this is pipetted with a 10-mL sterile, plastic pipette until a homogeneous suspension was obtained.
- 3.11.5. The cells were counted using a Goryaev chamber.
- 3.11.6. The cells were then plated into new petri dishes plated at a density of 10-50 cells per $cm^2$ using a 10-mL sterile plastic pipette.
- 3.11.7. Medium was added to the needed volume (to 9-10 mL) to petri dishes using a 10-mL sterile plastic pipette.

4. Growth Medium Composition (per 100 mL)

| Name | Amount | Measurement Units | Manufacturer |
|---|---|---|---|
| F12 medium | 49 | mL | HyClone |
| DMEM medium | 49 | mL | HyClone |
| Gentamicin 4% | 250 | µL | Sigma |
| Glutamine | 2 | mM | PanEko |
| Fibroblast growth factor | 10 | ng/mL | ProSpec-Tany TechnoGene LTD |
| Heparin | 8 | U/mL | |
| FBS FetalClone III | 15 | mL | HyClone (SH3010903) |
| Insulin | 1 | µg mL | |
| Transferrin | 10 | µg mL | |

5. Characteristics of the MMSC Culture 5.1. During culturing, cells were checked constantly and carefully in regard to bacteria and microscopic fungi, and also for the presence of bacteriological and viral infections. For this purpose, after the third passage, a portion of cells during passaging were given to the certified laboratory for analysis. PCR analysis showed the cells were negative for HBV, HCV, CMV, HSV-1 and -2, *Toxoplasma gondii*, *Mycoplasma* and Epstein-Barr virus.

Figure 11:
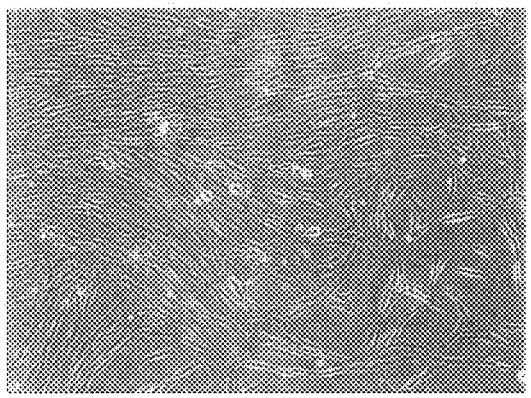
FIG. 11 is a light microscopy image of human mesenchymal stem cells.

5.2. Cell viability and morphology were assessed using a light microscope (FIG. 11).

5.3. Clonogenicity of the Culture

Figure 12:
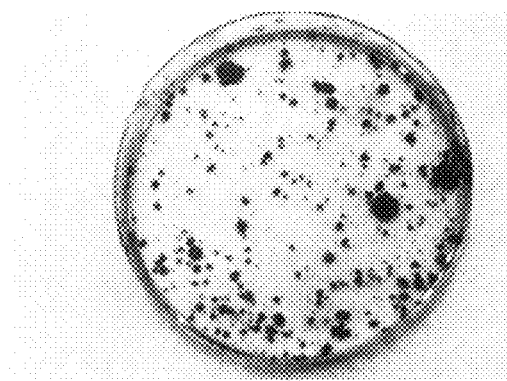
FIG. 12 is an image of human mesenchymal stem cell colonies after 10 days in culture and staining with an alcohol solution of 0.5% crystal violet.
Figure 13A:
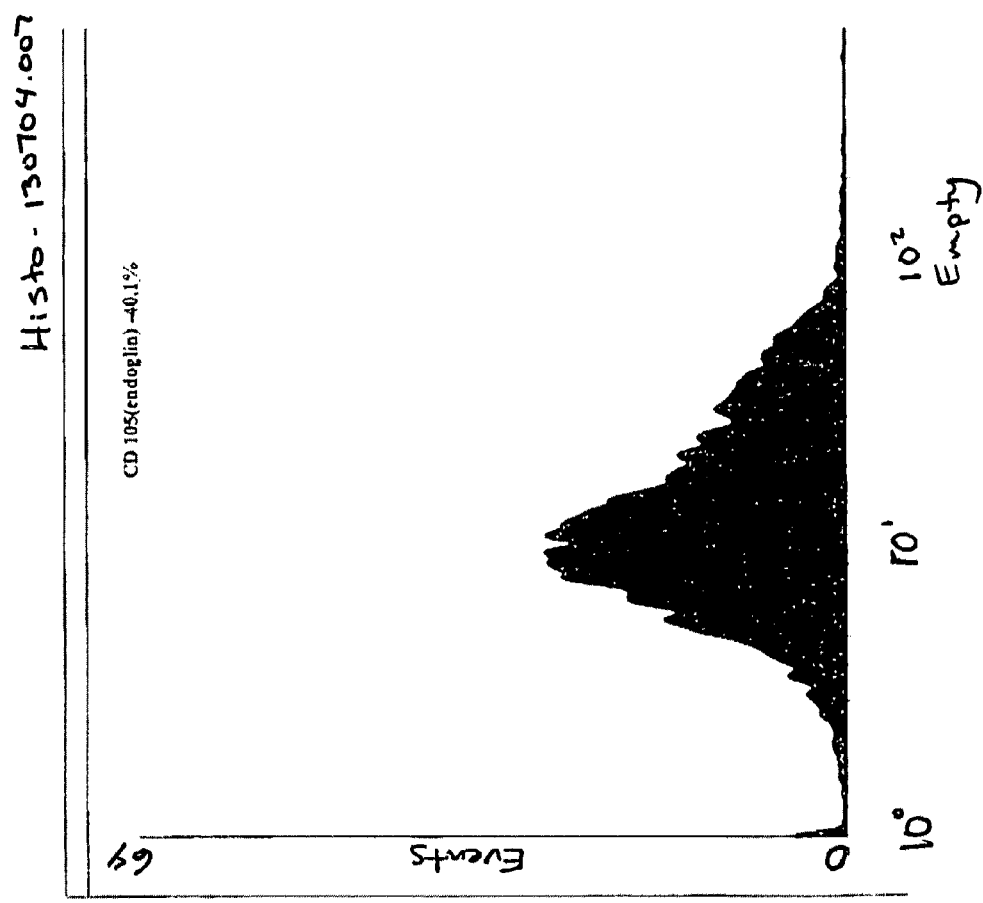
FIGS. 13*a-f* are graphs showing the expression profiles of human mesenchymal stem cells for CD105, CD90, CD44, CD34, HLA-ABC and HLA-DR respectively.
Figure 13B:
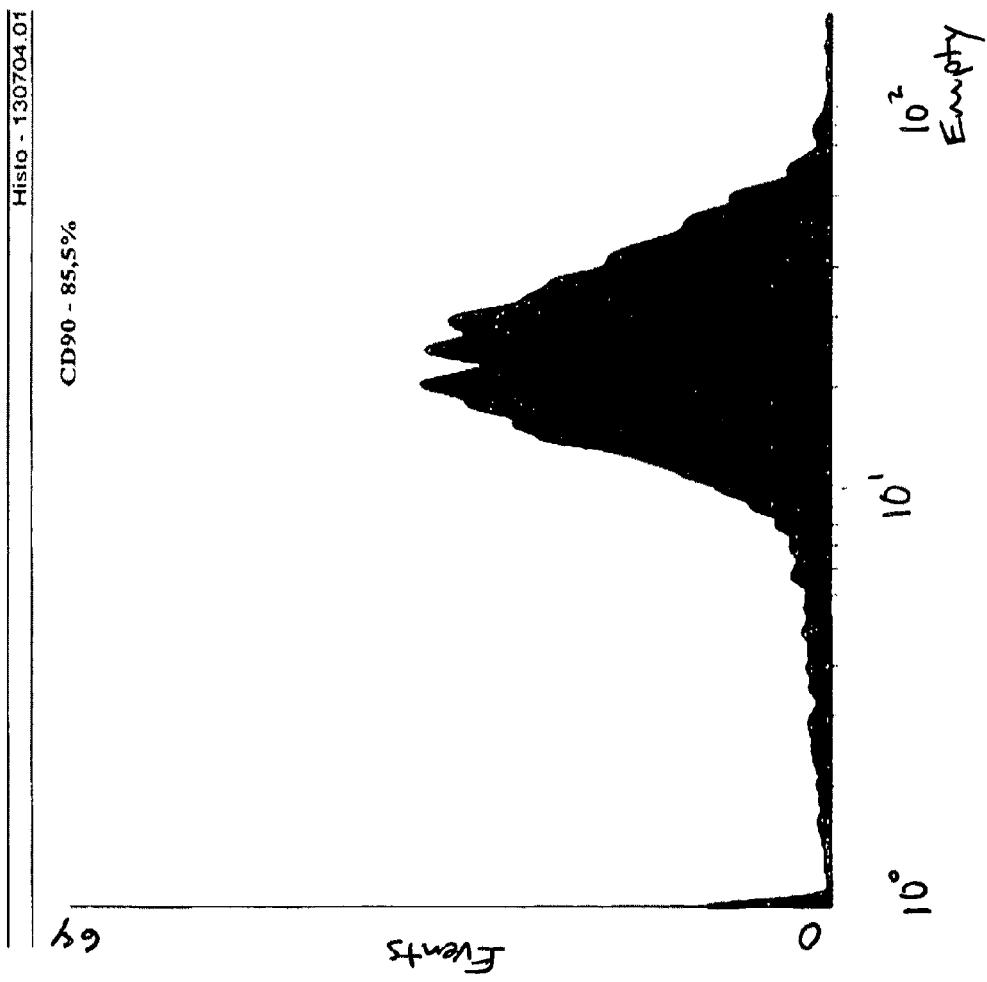
Figure 13C:
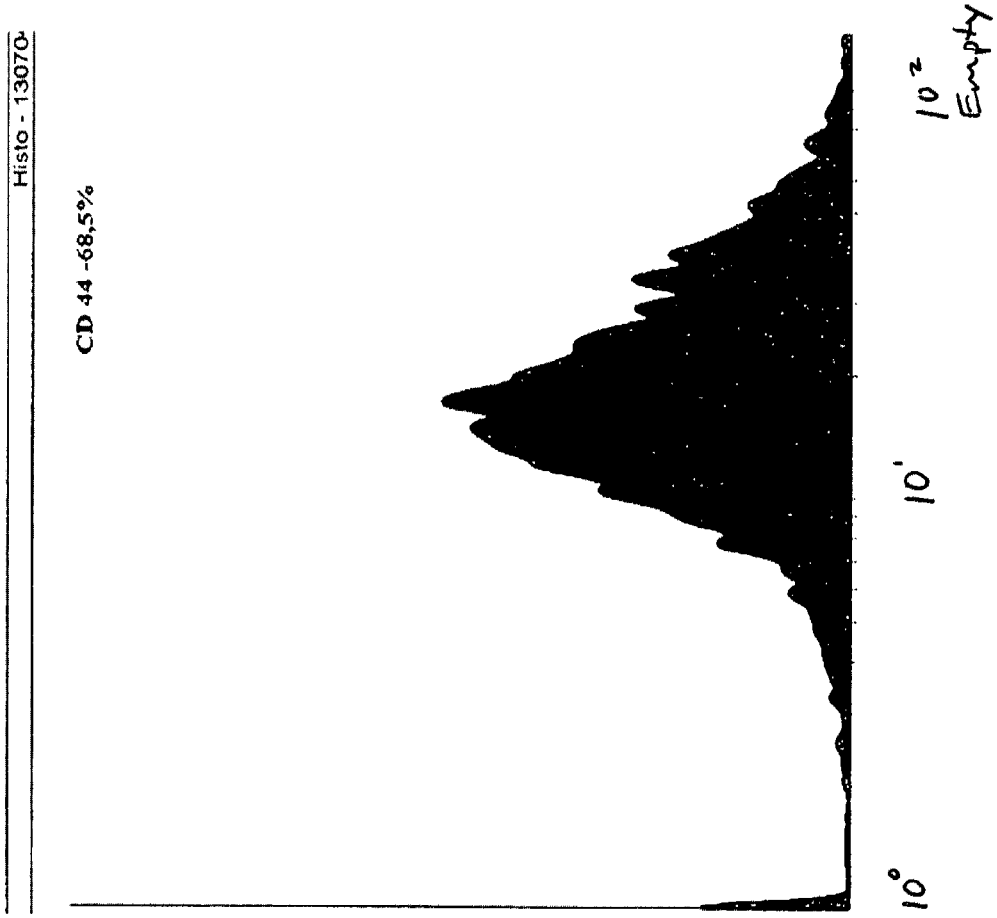
Figure 13D:
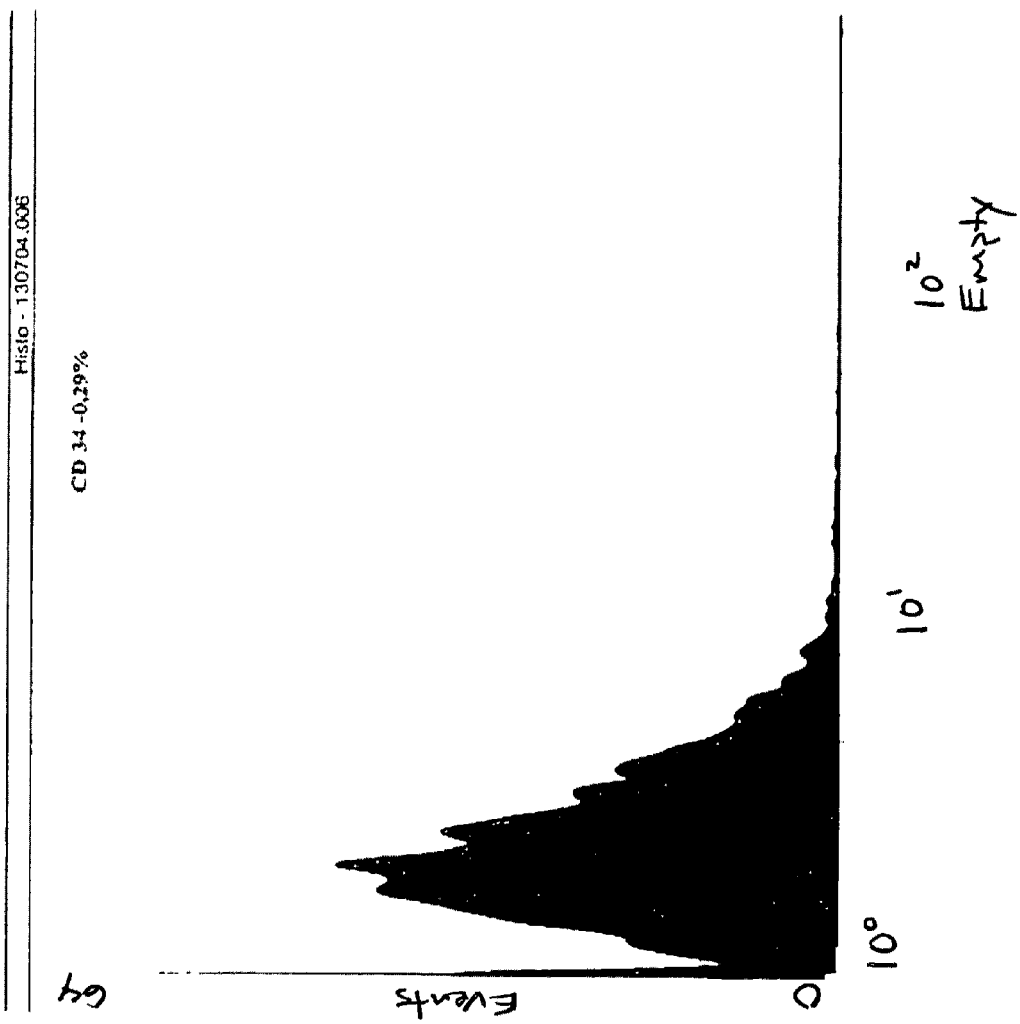
Figure 13E:
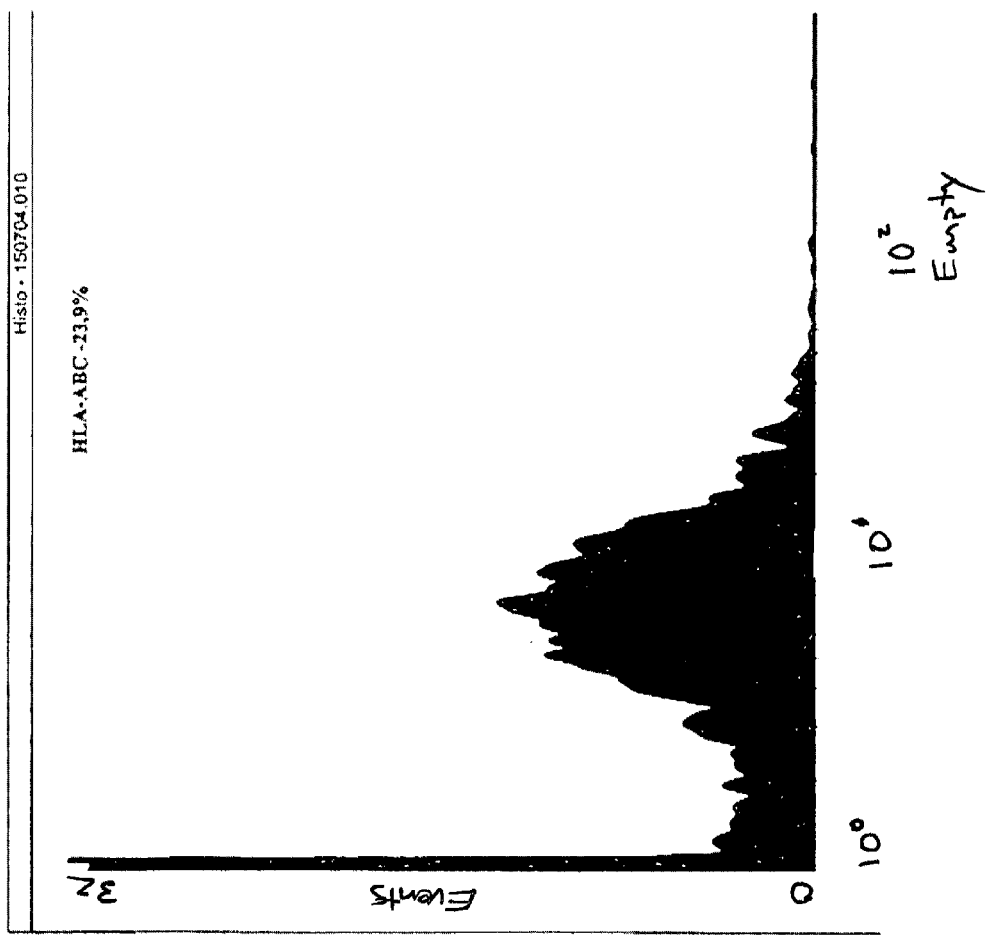
Figure 13F:
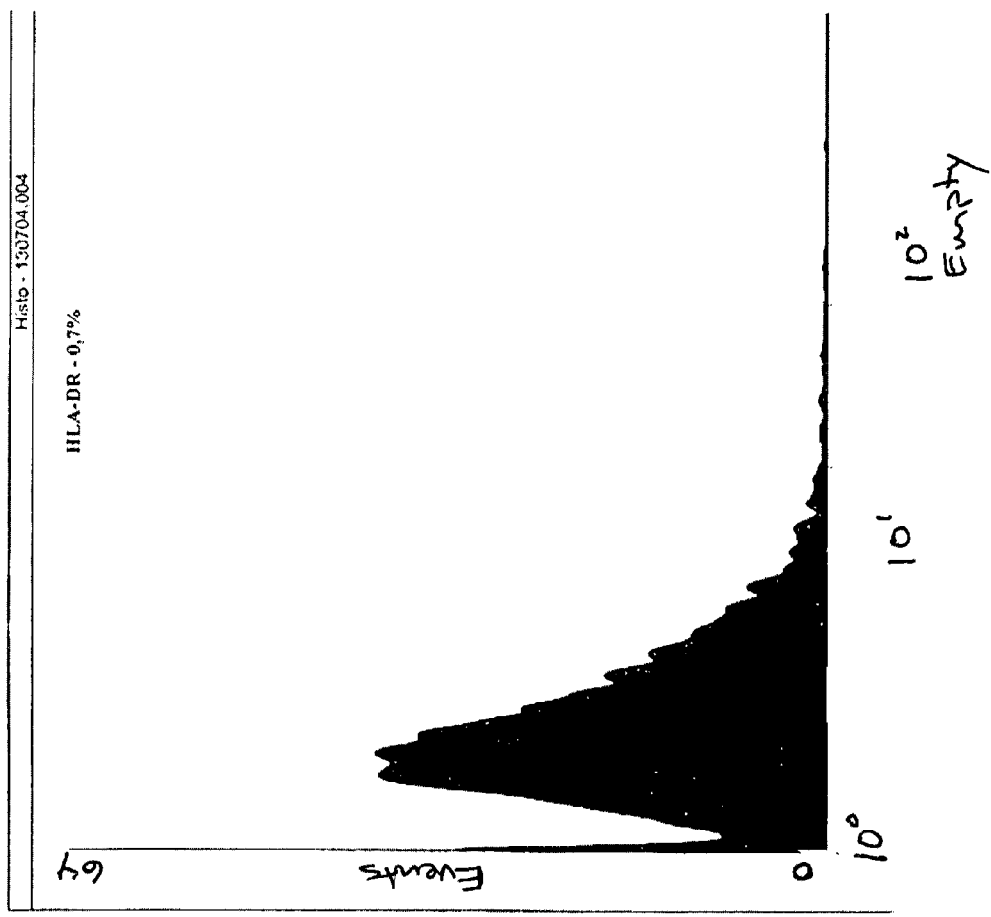
Figure 19:
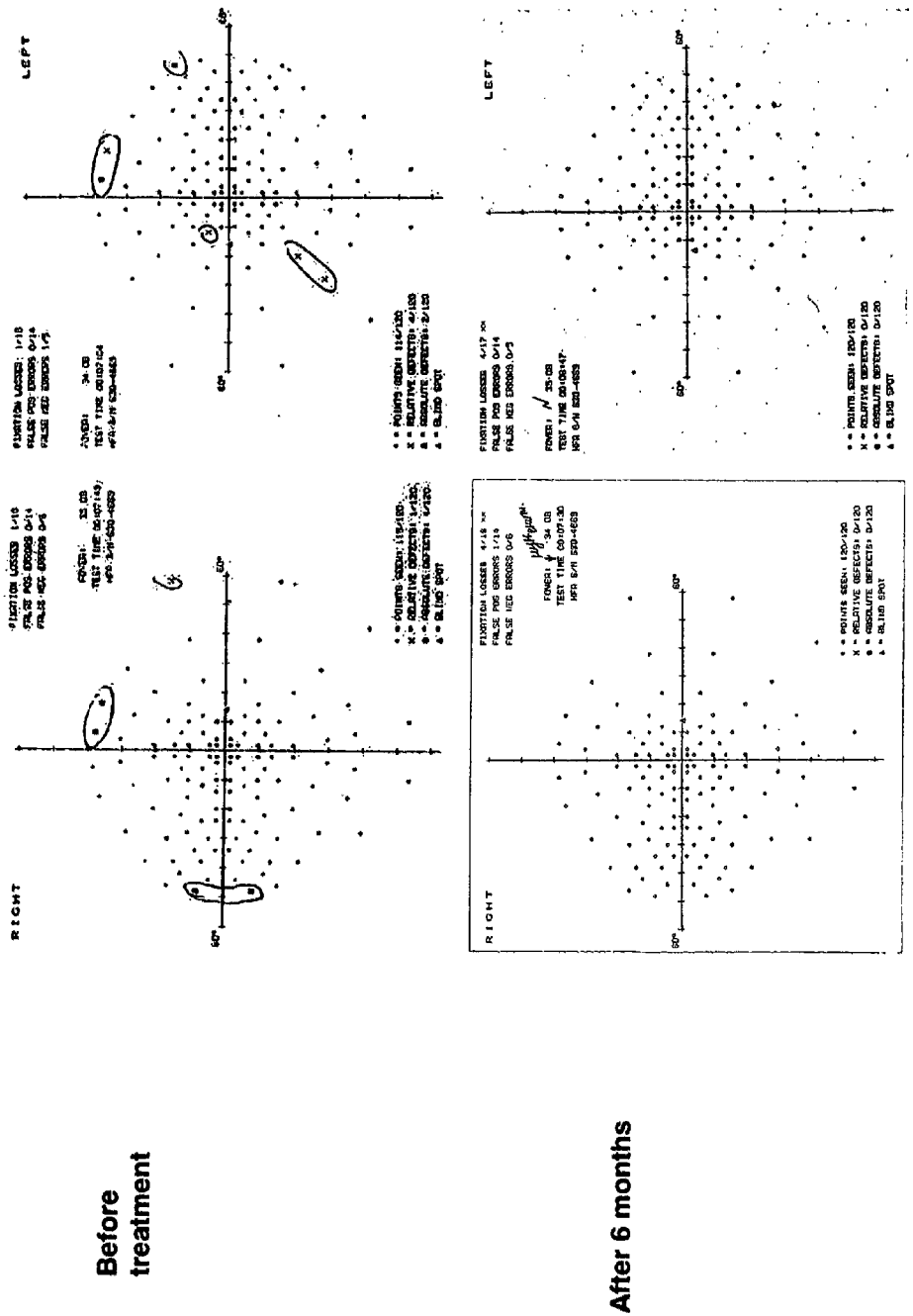
FIGS. 19-21 show the pre- and post-operative results for Patient 1 after intravenous injection of mesenchymal cells.
Figure 20:
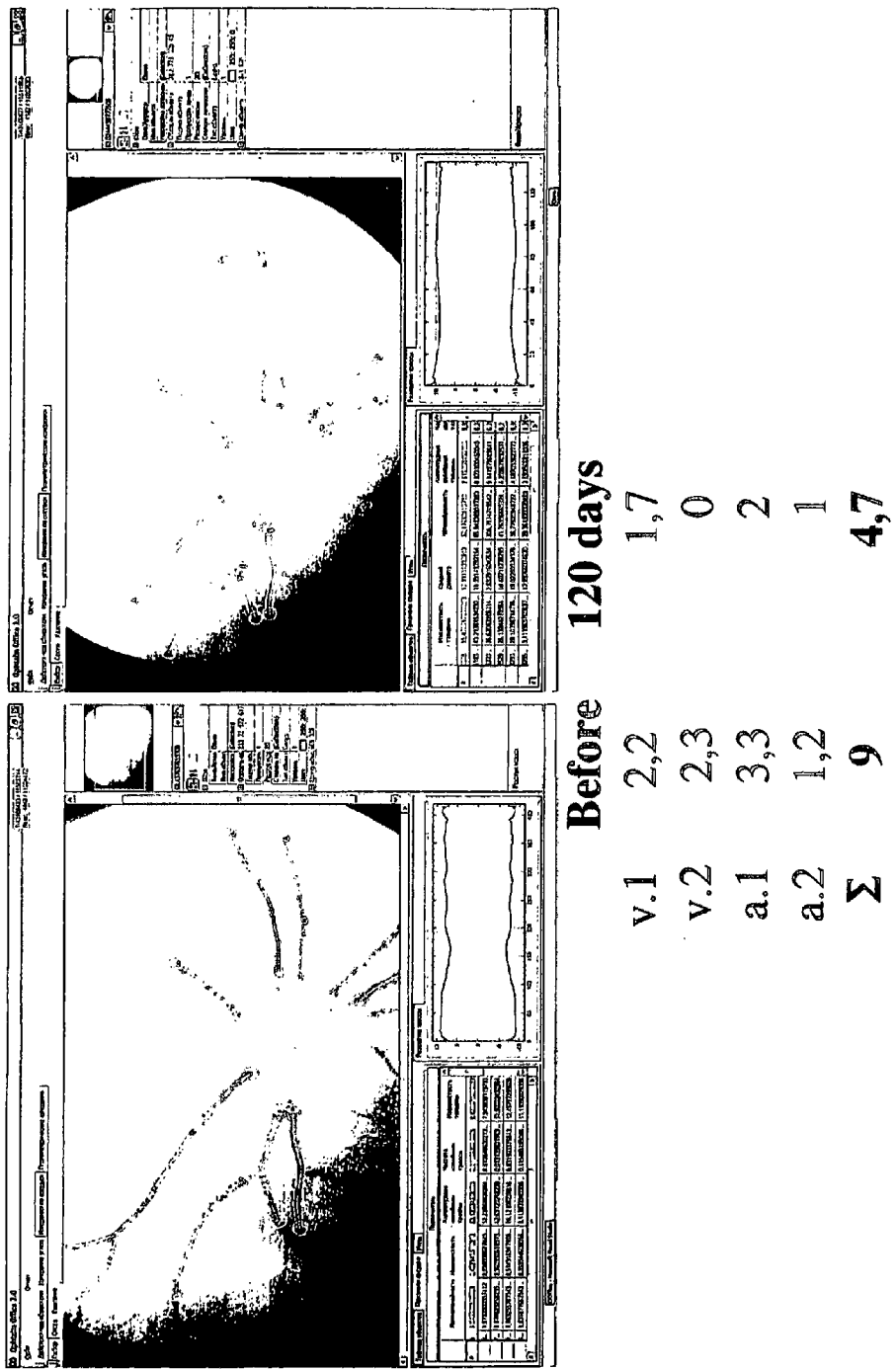
Figure 21:
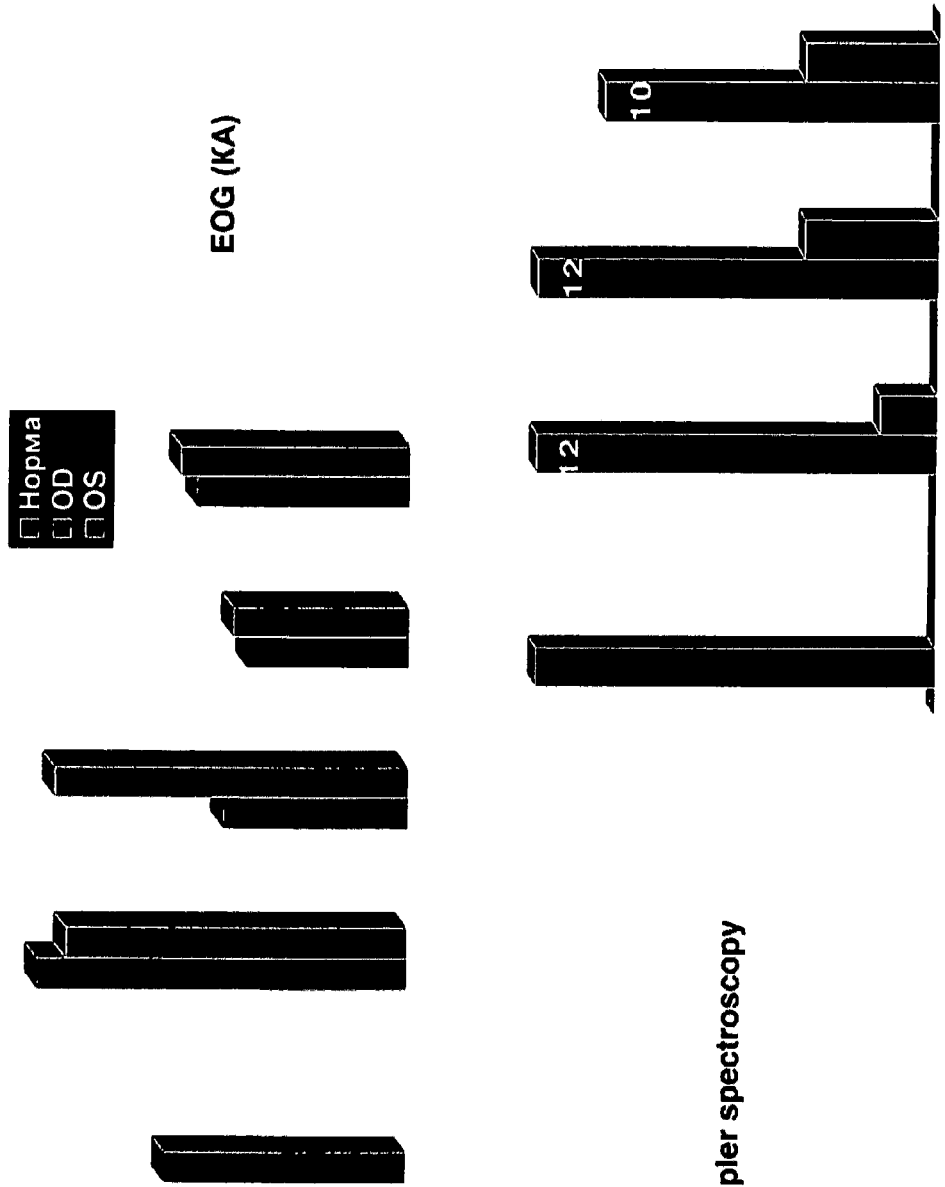
Figure 22:
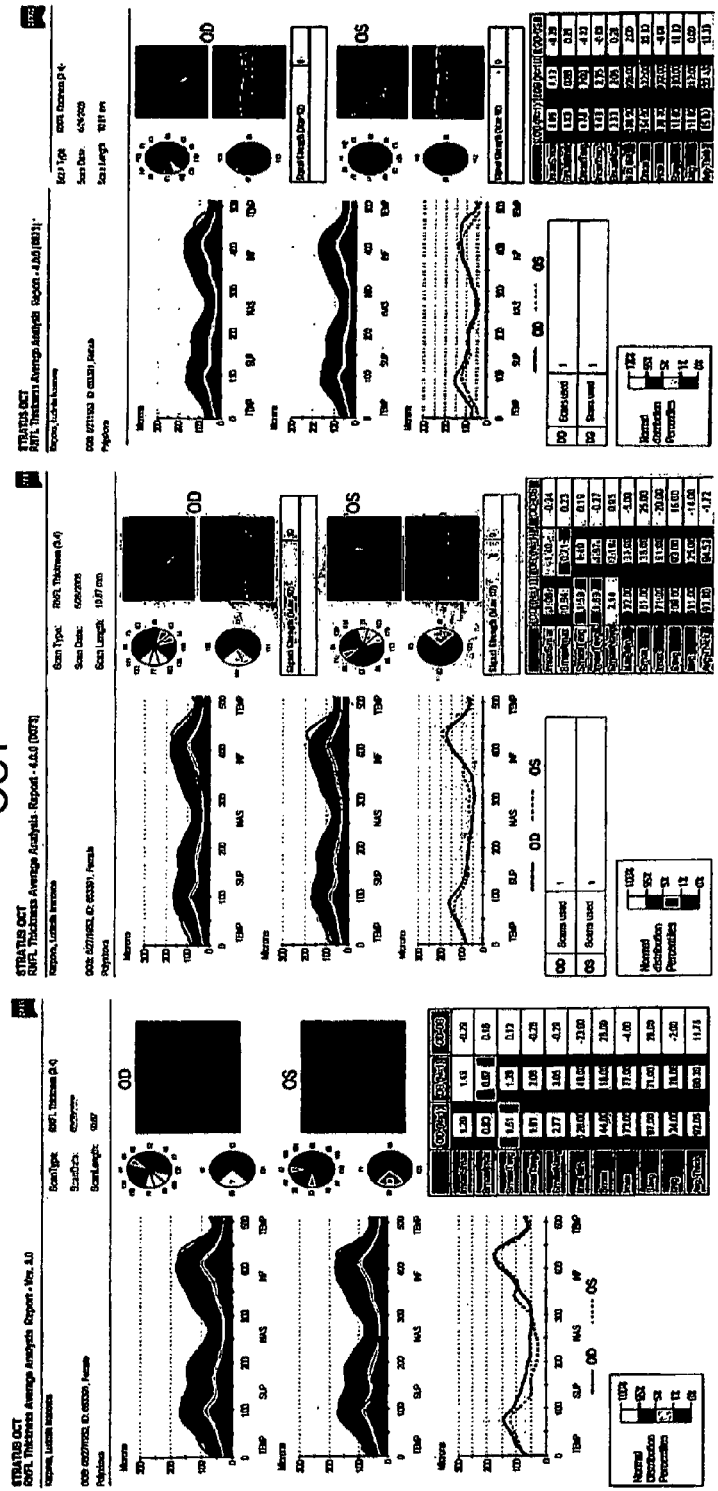
Figure 23:
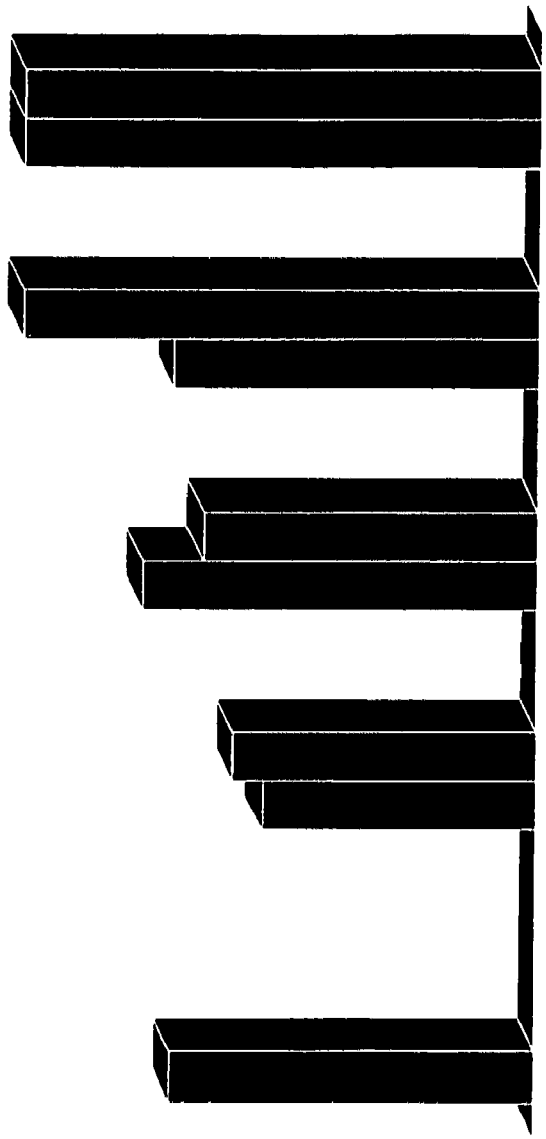
Figure 24:
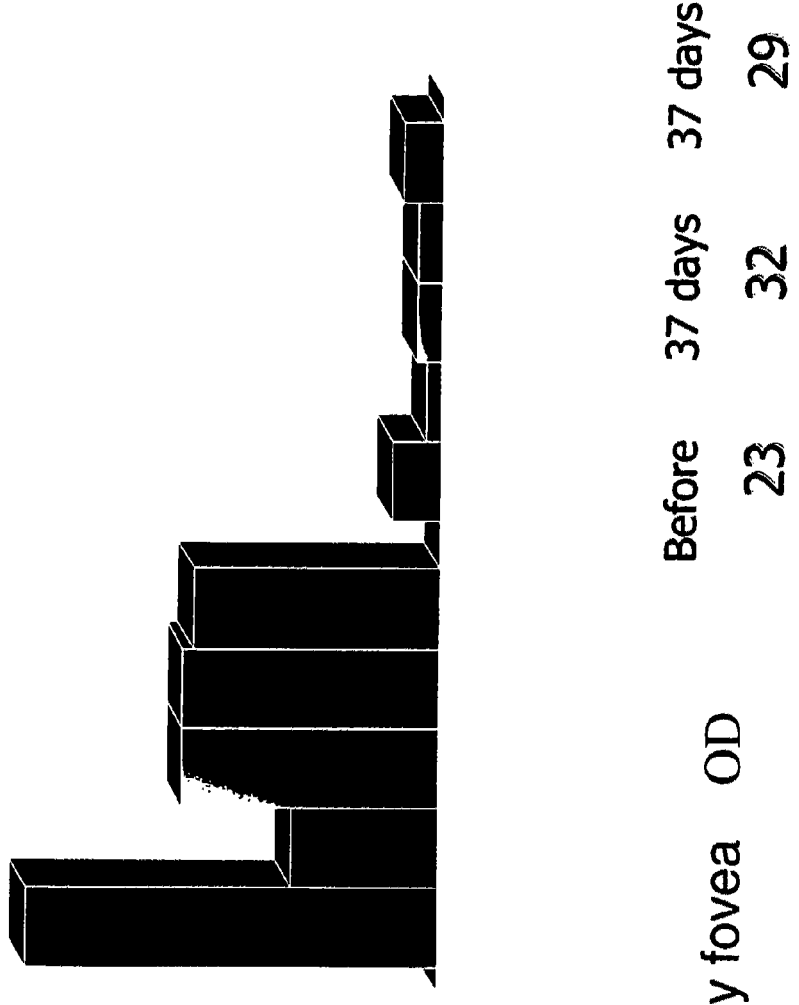
Figure 25:
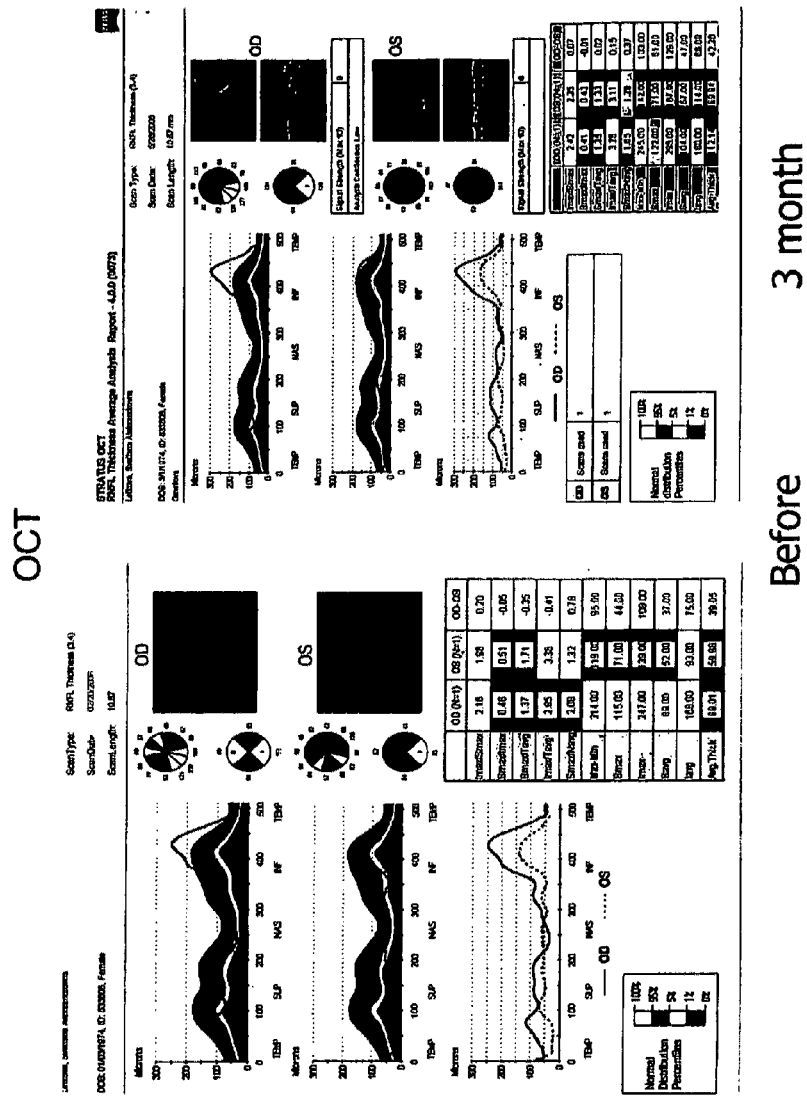
Figure 26:
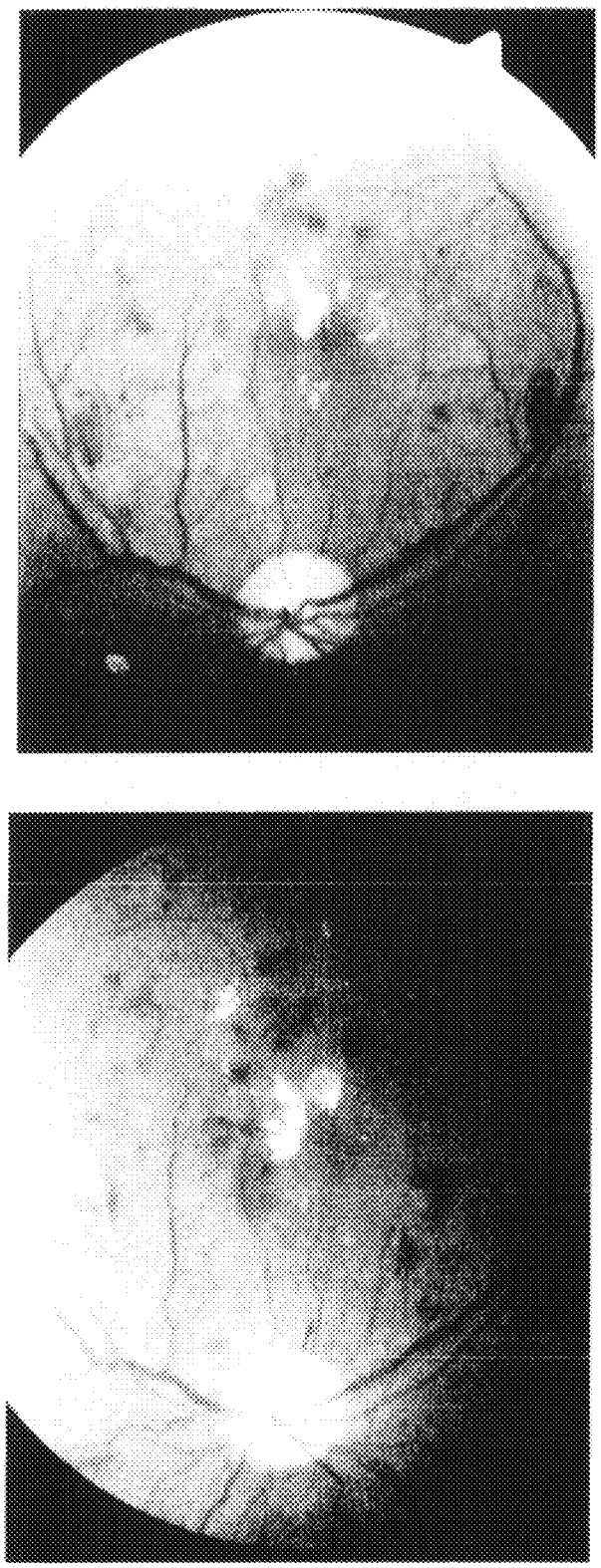
Figure 27:
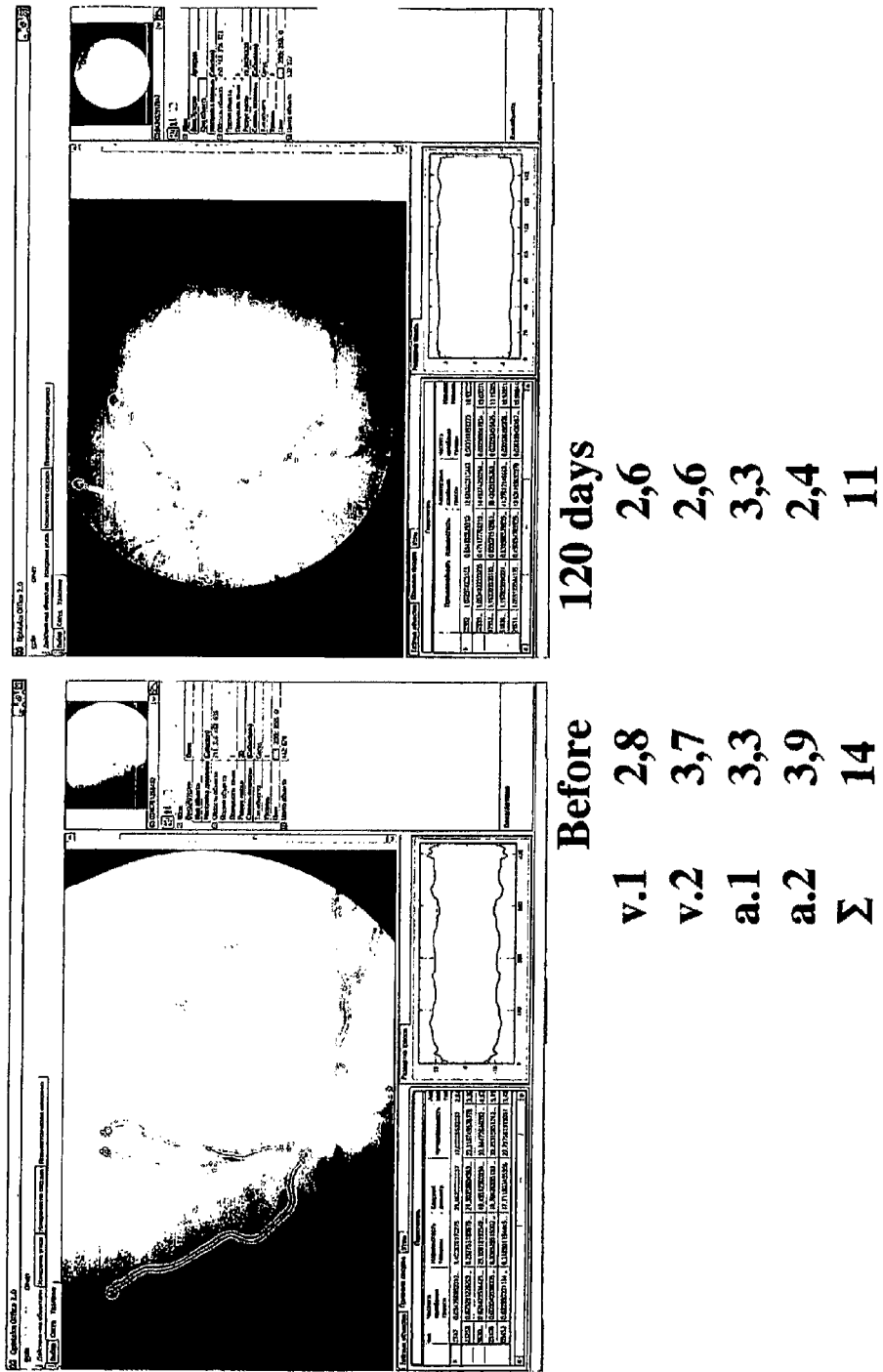
Figure 28:
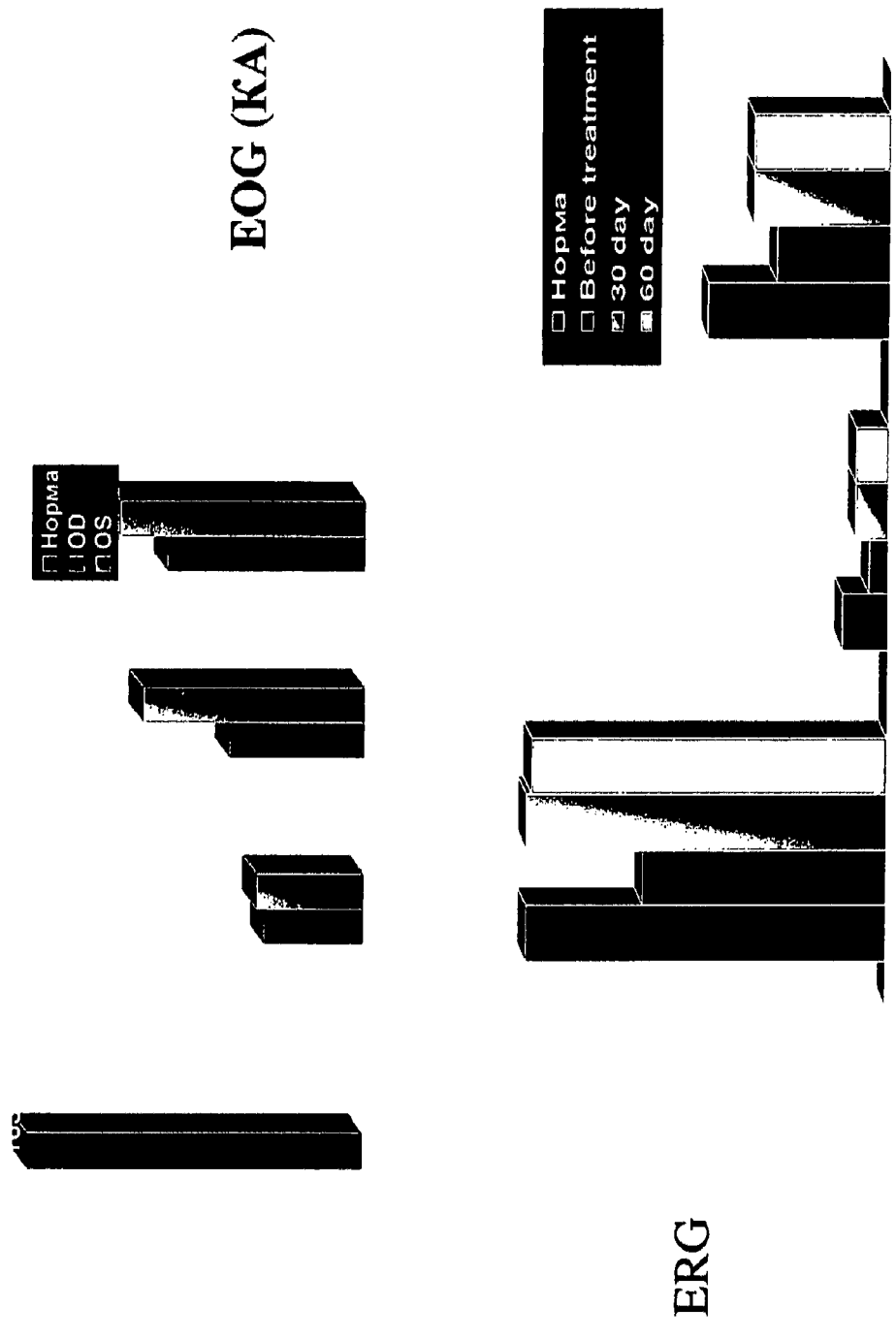
Figure 29:
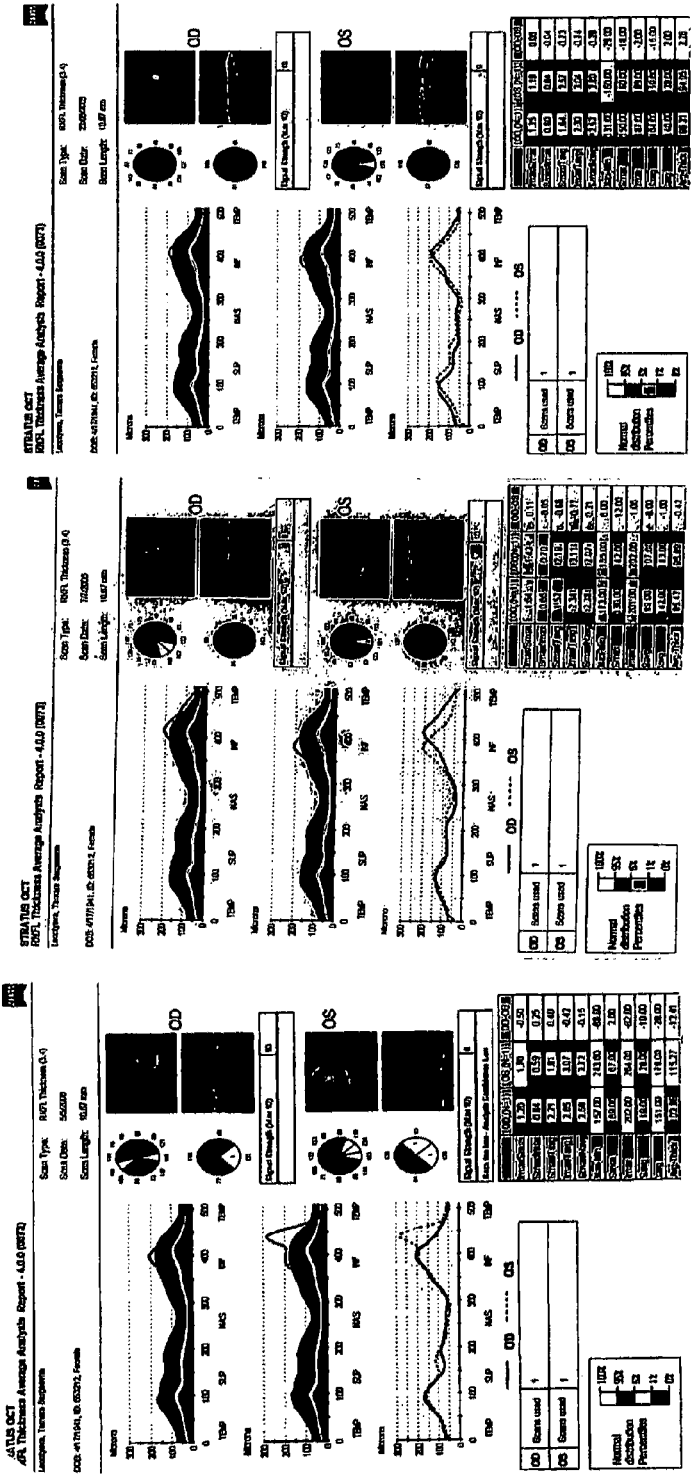
Figure 30:
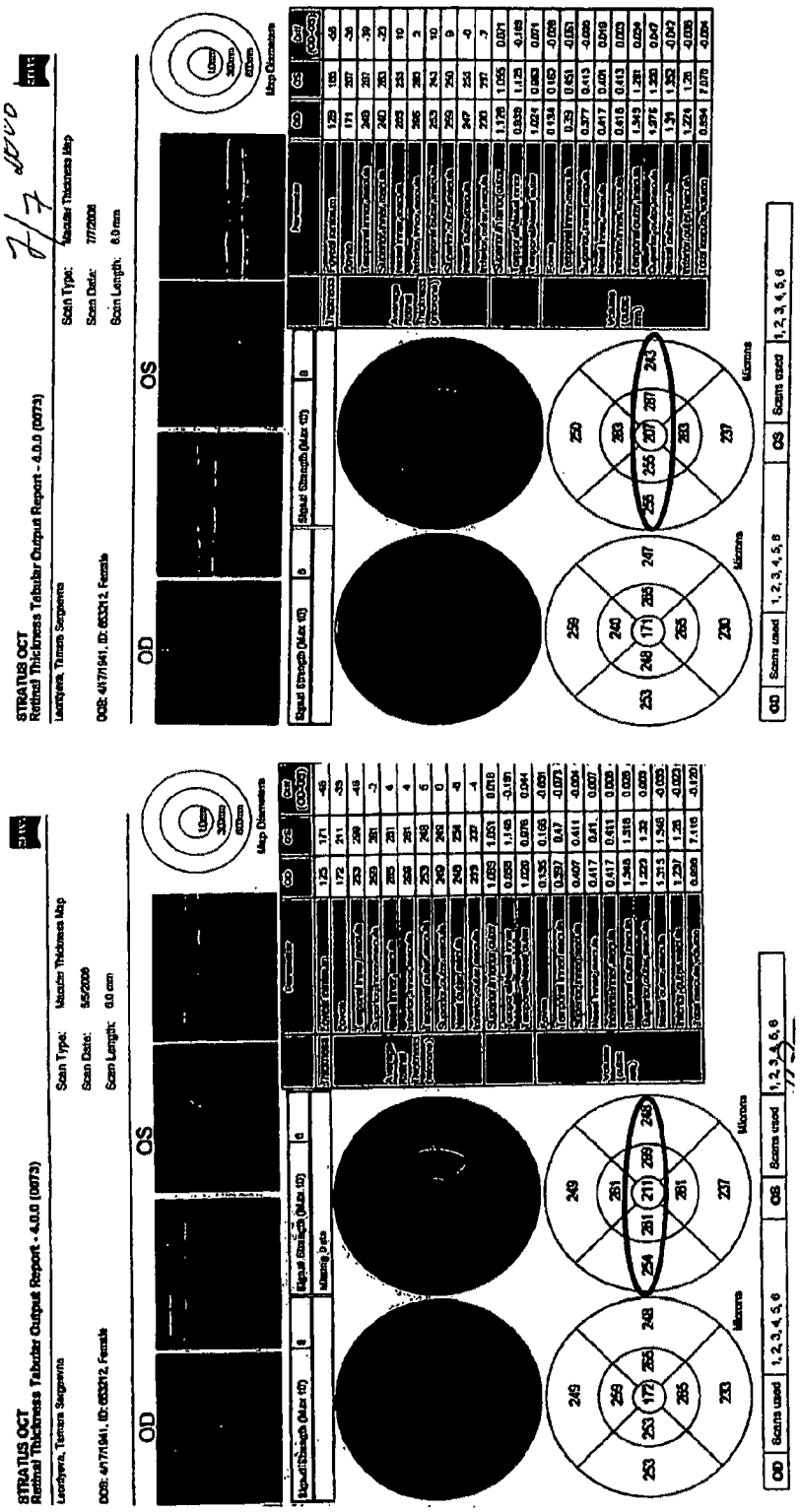
Figure 31:
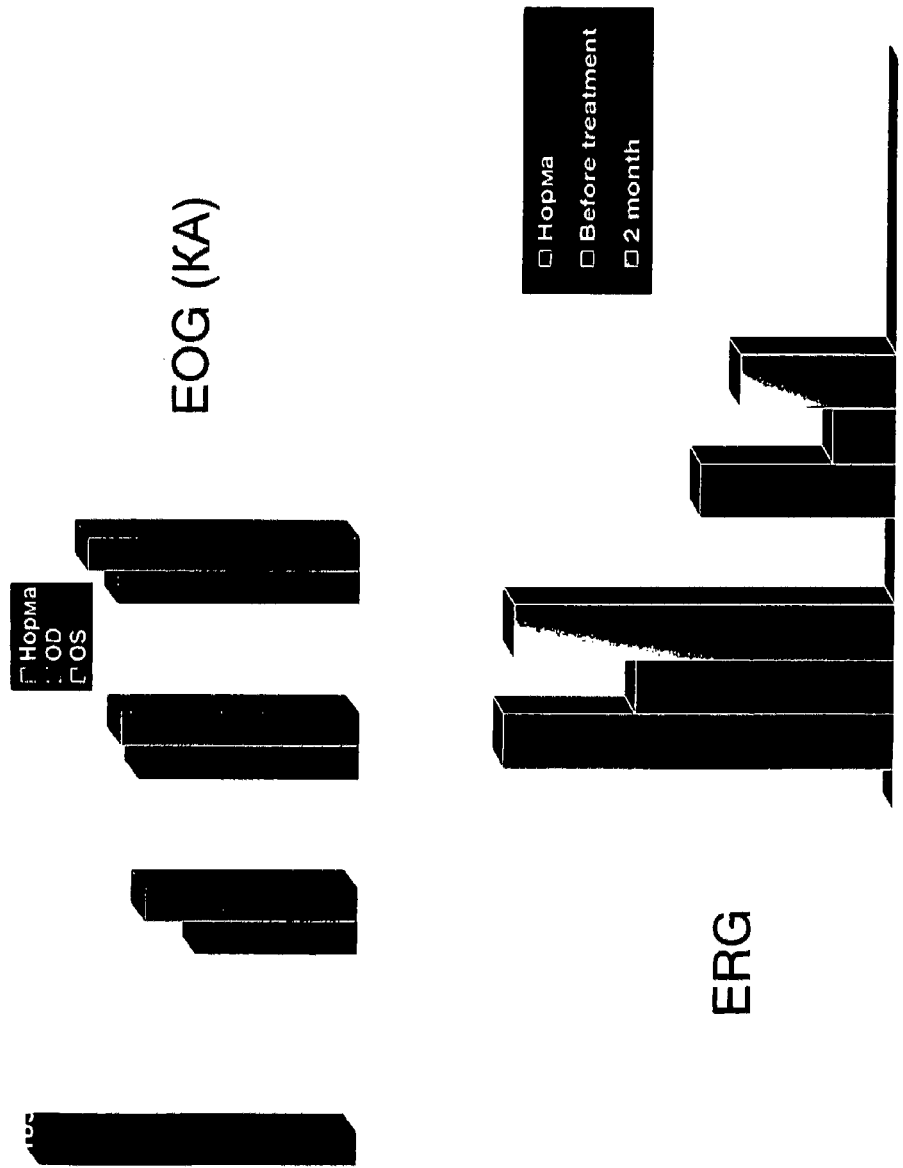
Figure 32:
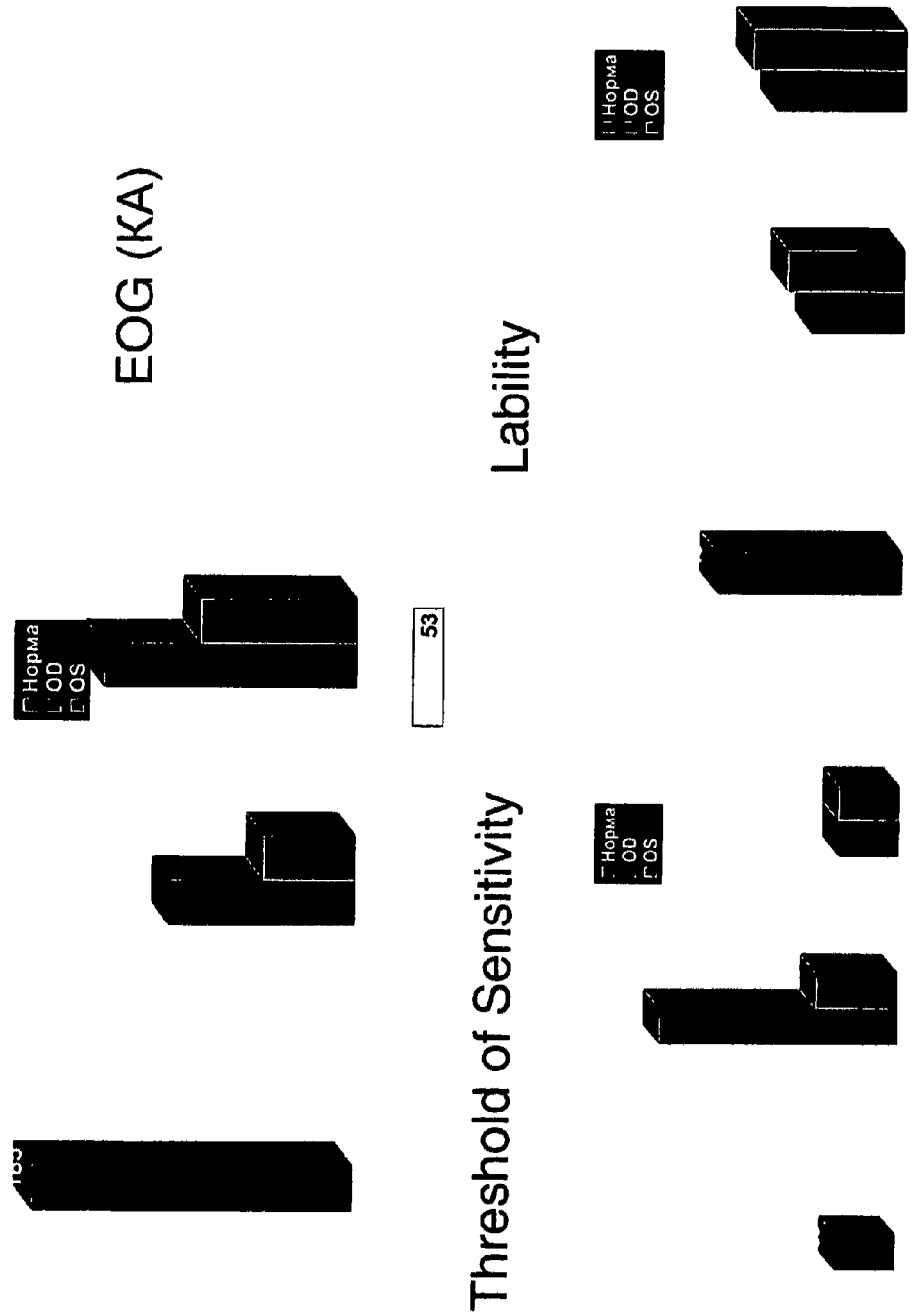
Figure 33:
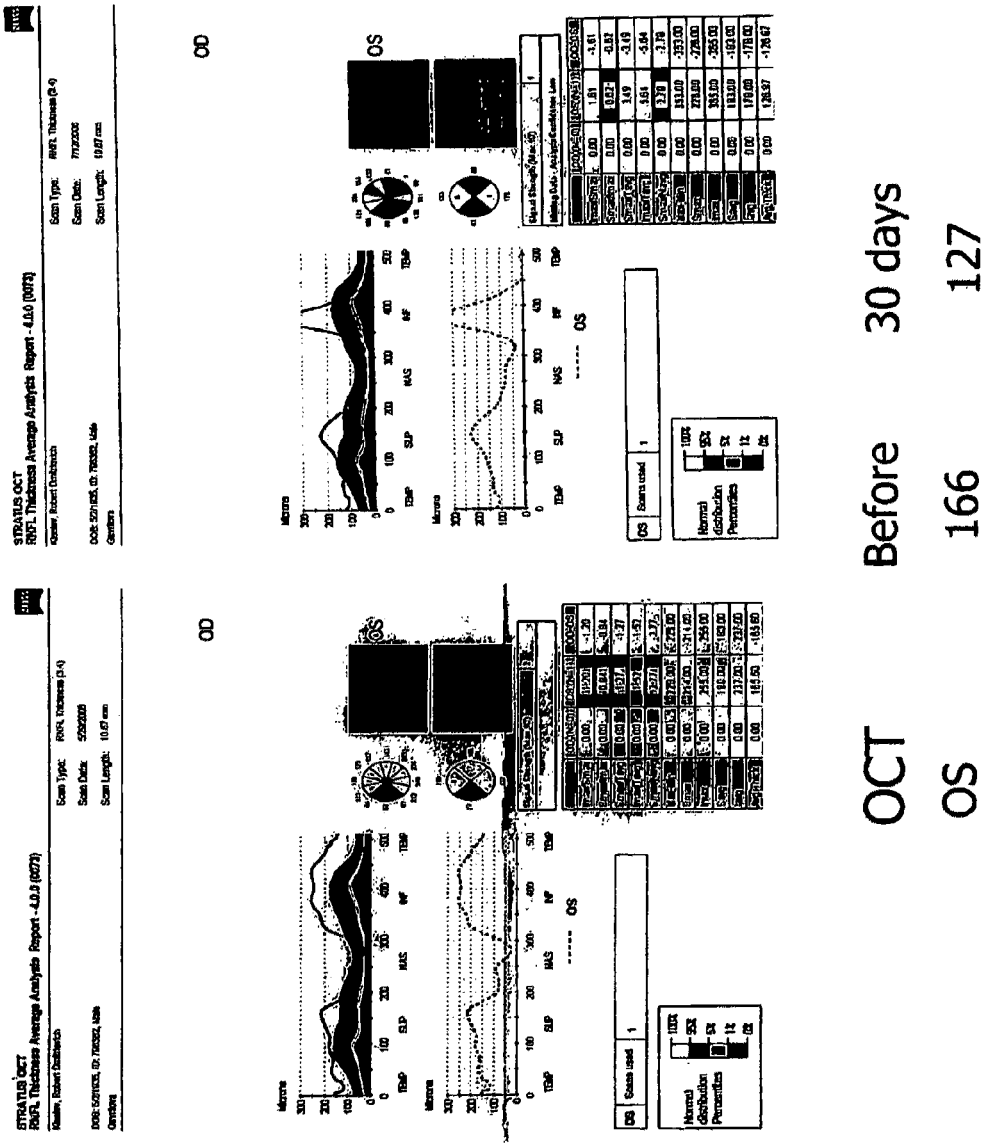
Figure 34:
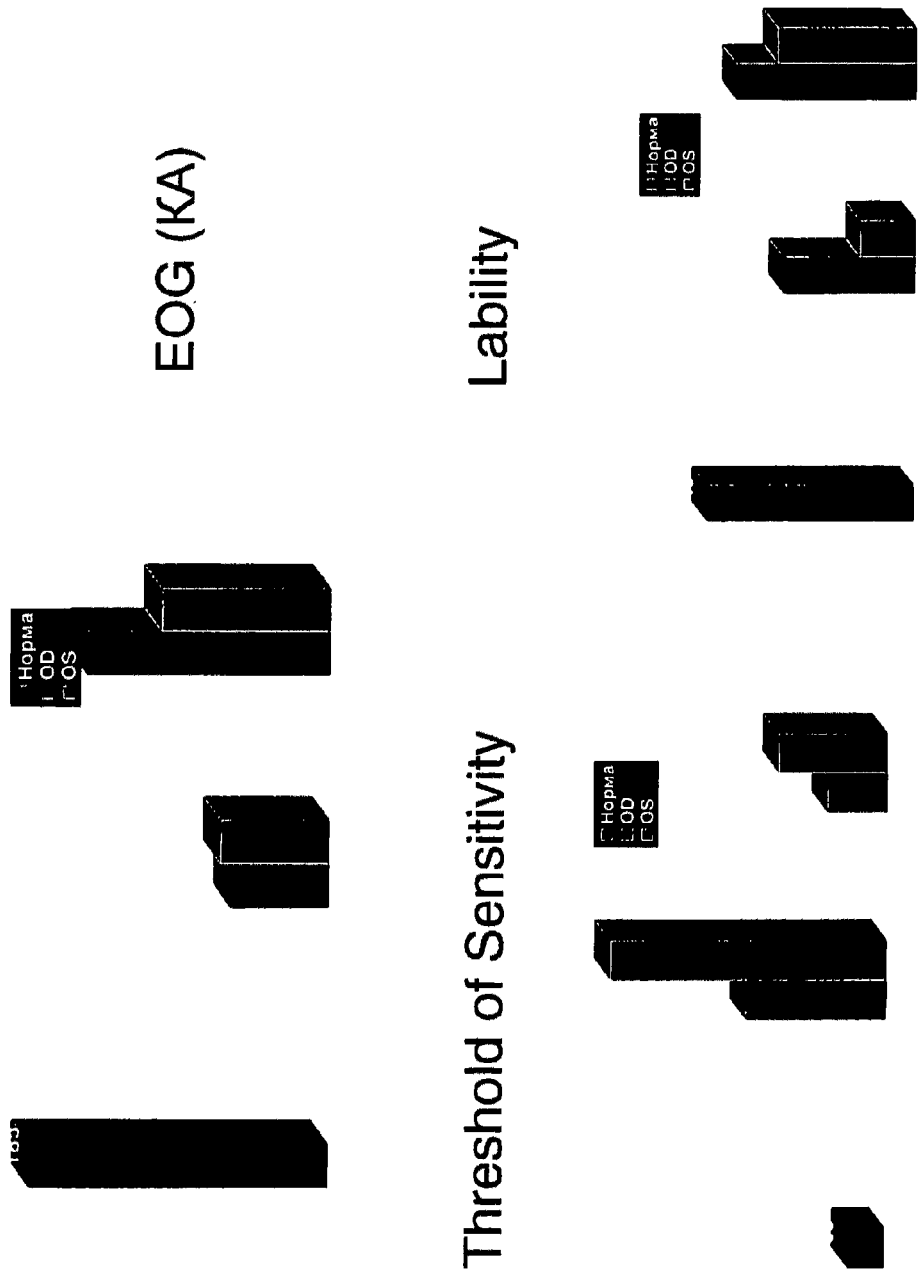

After 10 days of culturing after low density plating (3-4 cells per 1 $cm^2$), the colonies were counted in the control dish by staining with an alcohol solution of 0.5% crystal violet. FIG. 12 is an image showing the colonies with positive staining.

5.4. Cytofluorometric Analysis (FACS)

To perform the analysis, during passaging a portion of the cells was suspended in PBS, pH 7.4, after trypsinization at a concentration of 100,000 cells/mL, fixed in 1% methanol at 4° C. for 10 minutes, and then washed. Nonspecific binding was blocked by incubation in 1% BSA and 0.1% goat serum for 1 hour at room temperature. Then, the cells were washed in three volumes of phosphate-buffered saline and centrifuged: the precipitate was suspended in a 0.5% working solution of primary antibodies to 1% BSA with 0.1% goat serum. After incubation for 40 minutes at 4° C., the cells were washed with phosphate-buffered saline, pH 7.4. Mouse monoclonal antibodies (McAb) to CD44, CD90, CD105, CD34, HLA ABC, and HLA DR purchased from PharMingen and Chemicon were used. Nonspecific mouse (rabbit) IgG from the same companies was used as the negative control. Incubation with anti-species antibodies, labeled with FITC or phycoerythrin was performed for 20 minutes. Cells were then washed in phosphate-buffered saline, pH 7.4, and analyzed in a volume of 1 mL in a flow cytofluorometer FACS Calibur (BD Biosciences). Results were analyzed using the program MDI 2.8.

Individual populations were identified in the flow cytofluorometer with use of the combination of McAb for differentiation and activation markers. The number of apoptotic cells was determined using McAb to CD95 (FAS/APO-1 antigen), and the number of hematopoietic cells using McAb to CD34. The functional activity of cellular immunity was evaluated based on the number of cells, expressing the receptor to IL2 (IL2R-CD3+, CD25+) and HLA-DR antigen on their surface, and also based on the number of activated cells (CD71+, CD38+) and activated NK (CD8+, CD 16+).

The primary marker of hematopoietic cells (CD34) and HLA DR in clonal cultures MMSC from bone marrow was expressed by less than 1% of cells (at the level of the negative control). The largest cell population (80-92%) was stained by antibodies to CD90 (80-95%), CD44 (60-75%), and endoglin CD105 (about 50%). Antigens MHC1 (HLA-ABC) were present on the surface of 5-30% of the cells. The fraction of positive cells changed minimally during passaging, but remained unvaryingly low overall (see FIGS. 13a-f).

6. Cryopreservation

Before cryopreservation, a portion of the cells was used for the contamination test (final infection check), and the rest were frozen.
- 6.1. The condensed medium was removed from petri dishes with the confluent monolayer culture using a 10-mL sterile plastic pipette.
- 6.2. The cell culture was washed three times with Versene solution using a 10-mL sterile pipette.
- 6.3. 2 mL of trypsin solution was added to a petri dish using a 10-mL sterile plastic pipette, and the dish was incubated at 37° C., 5% $CO_2$ for 10 minutes.
- 6.4. The suspension obtained after incubation was homogenized using a 10-mL sterile plastic pipette.
- 6.5. Up to 5 mL of nutrient medium was added to the suspension using a 10-mL sterile plastic pipette and the suspension was homogenized using a 10-mL sterile plastic pipette.
- 6.6. The cells were counted using a Goryaev chamber.
- 6.7. The suspension was transferred to a 15-mL centrifuge tube using a 10-mL sterile pipette and diluted to 1.0 mL with Hank's solution using a 10-mL sterile pipette.
- 6.8. The suspension was centrifuged for 10 minutes at 1000 rpm.
- 6.9. The supernatant was removed using a 10-mL pipette, and the cells were resuspended in the medium for freezing (human umbilical blood serum+7% dimethyl sulfoxide) at a concentration of 10 million cells per 1 mL of the medium for freezing.
- 6.10. The cell suspension was transferred to 5-mL cryotubes using a 5-mL pipette.
- 6.11. The cryotubes were labeled according to the established standard.
- 6.12. The material was frozen to −80° C. in a programmable low-temperature freezer.

7. Characteristics of the Biotransplant

A freshly obtained cell culture or a culture after its cryopreservation was used as the biotransplant.

7.1. Composition of a Biotransplant

The cell biotransplant was a sterile suspension of autologous or allogenic mesenchymal stem cells, resembling fibroblasts, in physiological solution. The content of one flask of cell suspension was designated for only one patient and only for a single use. The amount of injected cells in a suspension and the volume were determined individually depending on specific objectives. The biotransplant was prepared for a specific patient 1-3 hours before the scheduled injection.

7.2. Amount and Fraction of Viable Cells

In preparing the biotransplant from a freshly prepared culture, the cell viability was at least 95%, which was checked with a test using trypan blue. In preparing a biotransplant from a cryopreserved culture, the cell viability after threefold rinsing was at least 90%.

Example 2

Immunophenotyping MMSCs

Probe Preparation. Cells suspended in PBS at concentration $1 \times 10^3$ cells/ml, fixed in 1% of methanol at 4° C. for 10 min, after this they were washed. Non-specific binding was blocked by incubation in 1% BSA and 0.1% goat serum for 1 hour at room temperature. After this, cells were washed in triple volume of PBS, centrifuged and the pellet suspended in 0.5% primary antibodies solution.

After incubation, cells were washed in PBS for 40 min. The mouse antibodies used were manufactured by Santa Cruz Biotechnology and Chemicon. As a negative control, nonspecific mouse antibodies were used. The incubation with anti-mouse antibodies, marked with FITC and PE was performed for 20 min. After this, cells were washed in PBS in volume of 1 ml and analyzed using FACS Caliber (BD Biosciences).

Results

Marker Positive cells (%)
HLA-ABS-24.9
HLA-DR 0.7
CD34-0.29
CD45-0.76
CD44-78.4
CD90-85.7
CD105-60.5
Vimentin-96.6
F(ab)-3.6

Example 3

Functional Description of MMSC

The functional activity of a MMSC culture was evaluated through the ability of the cells to differentiate into mesodermal cell lines (adipose geneses, osteogeneses, chondrogeneses, and miogeneses), under standard conditions, described for differentiating of mesenhymal stem cells, derived from bone marrow (DiGirolamo C. M., Stokes D., Colter D. C. et al. Br. J. Hematol. 1999, 107, 275-281; Sekiya I., Larson B., Smith J. et al. Stem Cells, 2002, 20, 530-541). FIG. 1 presents results obtained for the differentiation experiments.

Example 4

Biotransplant Preparation

Cell cultures were checked for the presence of pathogens by submitting a fraction of the cell cultures to licensed laboratories for PCR and immunofluocytometry analyses. All cell cultures tested negative for the presence of pathogens.

The biotransplant was made using freshly prepared cell cultures, although cryopreserved cell cultures could be used. The cell transplant was prepared as a sterile suspension of freshly prepared MMSC in 0.9% PBS solution. The cell viability was at least 95% (transplant preparation for cryopreserved cells uses a cell viability of and no less than 80-85%).

The cell concentration and volume of the biotransplant was determined individually depending on type of disease and degree of disease symptoms. The biotransplant was prepared individually for the patient 2-4 hours prior to transplantation.

Example 5

Production of Neural Stem Cells

1. Donor Characteristic

The tissue donor of the neural tissue was tested for a variety of pathogens. PCR analysis for infection showed the mother's blood serum tested negative for the following infection markers: HIV-1 and -2; HPLV-I and II; HBV; HCV; CMV; HSV-1 and 2; *toxoplasma gondii; mycoplasma*; Epstein-Barr virus; *ureaplasma; Chlamydia*; and *treponema pallidum*. Bacteriological tests showed the neural tissue was free of staphylococci, streptococci and *neisseria gonorrhoeae*.

2. Preparation of a Primary Cell Suspension of Neural Stem/Progenitor Cells (NSPC)

Source material for the neural stem cell suspension was the neocortical primordium from the brain of human fetuses at gestation weeks 9-11.

Initial Treatment of the Material 2.1. Using a quarantine workstation, either the entire forebrain or its fragments were isolated from the fetus with the use of ophthalmic forceps and the meninges were carefully removed.

2.2. The forebrain tissue was placed in a 30- or 60-mm plastic petri dish using forceps, and washed with Hank's solution, containing antibiotics (1 g of cefazolin and 250 mg of amphotericin B per 450 mL of solution), by adding 45 mL of the solution using a 5-mL plastic pipette.

2.3. The material was then washed with 10 mL of Versene solution for 1 minute.

2.4. The Versene solution was removed, 1 mL of growth medium was added, and the material was mechanically dissociated by repeated pipetting using a 5-mL plastic pipette or a Pipetman with a 1-mL tip until a single cell suspension was obtained.

2.5. The obtained cell suspension was transferred to a 15-mL Corning centrifuge tube, 10 mL of medium was added, and the suspension was pipetted.

2.6. The suspension was centrifuged for 5 minutes at 700 rpm; the supernatant was removed with a 10-mL plastic pipette.

2.7. The cell pellet was suspended in 2 or 5 mL of growth medium (depending on the amount of isolated cells) using a Pipetman. The live cells were counted with the use of a 35-mm petri dish, a Pipetman tip, and a Goryaev chamber. The number of live and dead cells in the suspension was counted by adding trypan blue to the selected sample. Material with a viability of at least 60% was regarded as suitable for culturing.

2.8. Cells were seeded using a Pipetman with a 1-mL tip in 2 or 5 mL of growth medium in petri dishes, 30 or 60 mL in diameter, depending on the amount of the obtained cells.

FIG. 1 shows a phase-contrast microscopy (PCM), primary suspension of dissociated brain tissue cells from an embryo at 10 weeks of development. Seeding density was 1-2 mL of cells per 1 mL of medium.

3. Growth Medium (per 100 mL)

| Name | Amount | Measurement units | Manufacturer |
|---|---|---|---|
| F12 medium | 49 | mL | HyClone |
| DMEM medium | 49 | mL | HyClone |
| Gentamicin 4% | 250 | μL | Sigma |
| Glutamine | 2 | mM | PanEko |
| Fibroblast growth factor | 10 ng/mL | | ProSpec-Tany TechnoGene LTD |
| Epidermal growth factor | 10 ng/mL | | ProSpec-Tany TechnoGene LTD |
| Supplement N2 | 1 | mL | Gibco BRL |
| Heparin | 8 units/mL | | |
| FBS FetalClone III | 2 | mL | HyClone (SH3010903) |

4. Results of the Contamination Test

When negative results were obtained, the material was transferred from the quarantine workstation to the culturing workstation. If a positive result was obtained, the primary material was immediately destroyed and the workstation was sterilized.

5. Culturing and Characteristics of the Primary Culture 5.1. Culturing was carried out under standard conditions: at 37° C. in an atmosphere of 5% $CO_2$.

5.2. The medium was replaced once every 3 days.

5.2.1. Spent medium was removed from the petri dish using a 10-mL pipette.

5.2.2. The same volume of fresh growth medium was added to the dish using a sterile 10-mL pipette.

5.3. Composition of the growth medium

| Name | Amount | Measurement units | Manufacturer |
|---|---|---|---|
| F12 medium | 49 | mL | HyClone |
| DMEM medium | 49 | mL | HyClone |
| Gentamicin 4% | 250 | μL | Sigma |
| Glutamine | 2 | mM | PanEko |
| Fibroblast growth factor | 10 ng/mL | | ProSpec-Tany TechnoGene LTD |
| Epidermal growth factor | 10 ng/mL | | ProSpec-Tany TechnoGene LTD |
| Supplement N2 | 1 | mL | Gibco BRL |
| Heparin | 8 units/mL | | |
| FBS FetalClone III | 2 | mL | HyClone (SH3010903) |

Figure 2:
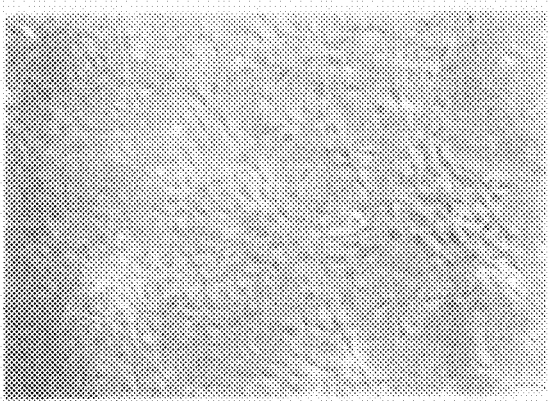
FIGS. 2 and 3 show microscopic images of neuroepithelial cells after 15 days, and 25 days in culture respectively.
Figure 3:
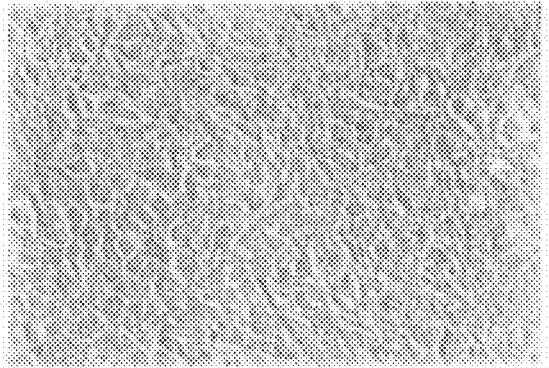

5.4. The time for obtaining a neuroectoderm cell culture ranged between 20 to 30 days. FIG. 2 shows neuroepithelial cells after 15 days in culture, while FIG. 3 shows neuroepithelial cells after 25 days in culture.

6. Culture Passaging 6.1. When cells reached confluence, the dishes with the cells were treated (washed) three times with Versene solution, then a trypsin solution (0.25%) was added to the dishes, and the dishes were left in an incubator for 3-5 minutes.

6.2. The sediment was resuspended and reseeded in new petri dishes or culture flasks at a 1:2 ratio in fresh growth medium.

7. Characteristics of the Passaged Culture 7.1. During culturing, the cultures were checked constantly and carefully in regard to bacteria and microscopic fungi, and also for the presence of bacteriological and viral infections. For this purpose, during passaging a portion of cells after passage 3-4 was given to the certification laboratory for PCR analysis. The sample tested negative for HBV, HCV, CMV, HSV-1 and 2, *toxoplasma gondii*, mycoplasma and Epstein-Barr virus.

7.2. Phenotyping of Passaged Cultures 7.2.1. Cytofluorometric Analysis (FACS)

To perform the analysis, during passaging a portion of the cells was suspended in PBS, pH 7.4, after trypsinization at a concentration of 100,000 cells/mL, fixed in 1% methanol at 4° C. for 10 minutes, and then rinsed. Nonspecific binding was blocked by incubation in 1% BSA with 0.1% goat serum for 1 hour at room temperature. Then, the cells were rinsed in 3 volumes of PBS and centrifuged; the pellet was suspended in a 0.5% working solution of primary antibodies to 1% BSA with 0.1% goat serum. The cells were incubated for 40 minutes at 4° C. and rinsed with PBS. Mouse monoclonal antibodies (Chemicon or PharMingen) were also used. Nonspecific mouse (rabbit) IgG from the same companies was used as the negative control. Cells were incubated with antispecies antibodies, labeled with FITC or phycoerythrin, for 20 minutes, then rinsed with PBS, and analyzed with a flow cytofluorometer "FACS Calibur" (BD Biosciences). Results were analyzed using the program "MDI 2.8."

|  | % |
|---|---|
| Neocr cells R(av)2 |  |
| HLA-DR | 2-10 |
| CD34 | 0.5-5 |
| CD45 | 0-1 |
| Nestin | 50-80 |
| Vimentin | 30-50 |
| b-Tubulin | 5-20 |
| GFAP | 5-10 |

7.2.2. Phase-Contrast Microscopy

Figure 4:
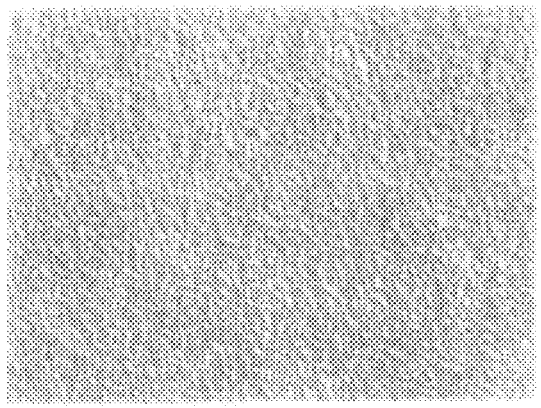
FIG. 4 shows a microscopic image of neuroepithelial cells after 5 passages.

FIG. 4 depicts a phase contrast image of neuroepithelial cells after 5 passages.

7.2.3. Immunocytochemical Analysis

To phenotype the obtained cell culture, an immunohistochemical analysis was performed based on the expression of nestin, type IV protein (from intermediate neurofilaments, expressed in multipotent neuronal stem cells), beta-tubulin III (marker for early neuroblasts), and acid glial fibrillar protein (GFAP) (a marker for glioblasts and mature glial cells).

Immunohistochemical analysis was performed using, as primary antibodies, anti-nestin (1:10), anti acid glial fibrillar protein (1:400), anti beta-tubulin III (1:100). Secondary antibodies were anti-goat conjugated with phycoerythrin, and anti-goat conjugated with fluorescein isothiocyanate (FITC).

Figure 5:
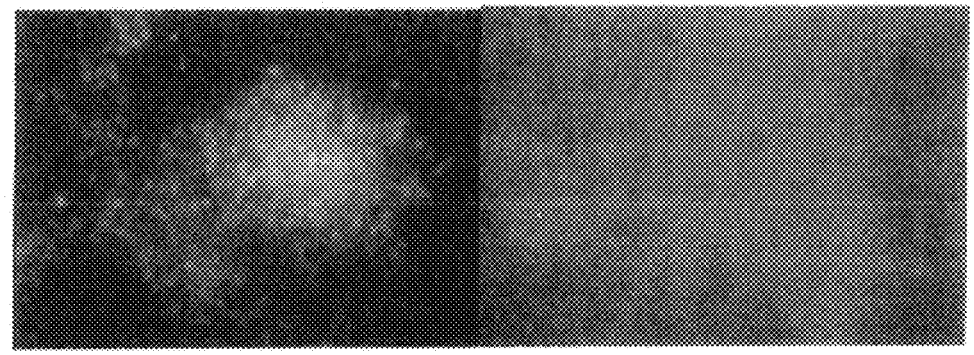
FIG. 5 shows a pair of microscopic images of neuroepithelial cells showing positive staining for nestin.
Figure 6:
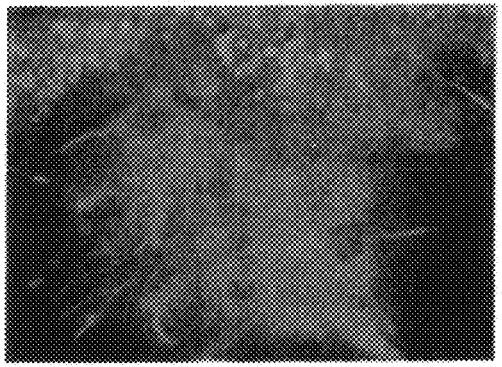
FIG. 6 is a microscopic image of neuroepithelial cells, with positive staining for beta-tubulin III.
Figure 7:
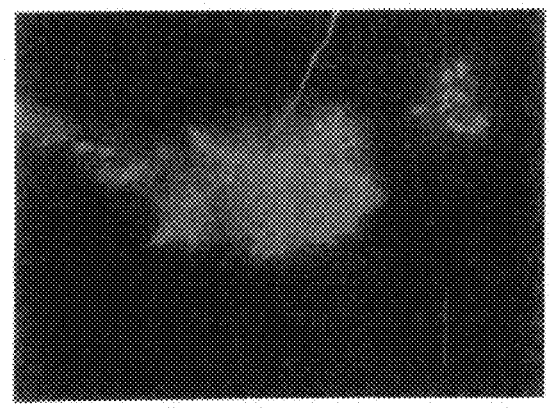
FIG. 7 is a microscopic image of neuroepithelial cells showing positive expression for glial fibrillary acidic protein (GFAP).

The neural stem cell culture showed expression of nestin (FIG. 5) and beta-tubulin III (FIG. 6) and GFAP (FIG. 7).

7.3. Cell Culturing Time

The number of passages depends on the state of the cells and their proliferative potential and is controlled by the expression of characteristic differentiation markers. The number of passages does not generally exceed 10 passages.

8. Cryopreservation

Before cryopreservation, a portion of the cells was used for a final contamination analysis and the rest of the cells were frozen.

8.1. The dishes or culture flasks with cells were treated (washed) three times with Versene solution, then a trypsin solution (0.25%) was added to the dishes, and the dishes were left in an incubator for 3-5 minutes.

8.2. The cells were carefully pipetted and the cell count was determined in a Goryaev chamber using a 35-mm petri dish and 1-mL tip for the Pipetman.

8.3. Cells were transferred by pipette to a 15-mL centrifuge tube and centrifuged for 6-7 minutes at 800-1000 rpm.

8.4. The supernatant was removed using a 10-mL pipette, and the cells were resuspended in the medium for freezing (human umbilical blood serum+7% dimethyl sulfoxide) at a concentration of 10 million cells per 1 mL of medium.

8.5. The cell suspension was transferred to 5-mL cryotubes using a 5-mL pipette.

8.6. The cryotubes were labeled according to the established standard.

8.7. The material was frozen to −80° C. in a programmable low-temperature freezer.

9. Characteristics of the Biotransplant

A freshly obtained cell culture or a culture after its cryopreservation was used as the biotransplant.

9.1. Composition of a Biotransplant

The cell biotransplant was a sterile suspension of allogenic neural stem cell progenitors (i.e. neural stem cells) in physiological solution. The content of one flask of cell suspension is designated for only one patient and only for a single use. The amount of injected cells in a suspension and the volume were determined individually depending on specific objectives. The biotransplant was prepared for a specific patient 1-3 hours before the scheduled injection.

9.2. Amount and Percentage of Viable Cells

In preparing the biotransplant from a freshly prepared culture, the cell viability was at least 95%, which is checked with a test using trypan blue. In preparing a biotransplant from a cryopreserved culture, the cell viability after threefold rinsing was at least 90%.

Example 6

Stem Cell Treatment

Seven patients with diabetes were enrolled in the study. The patients had varying degrees of diabetic retinopathy and diabetic optic neuropathy. The patients were observed at baseline and at day 2, day 8, day 14, day 30, day 60 and day 90 after treatment. Patients received one retrobulbar injection of $7 \times 10_6$ neural progenitor cells in at least one eye and one intravenous infusion of $100 \times 10_6$ mesenchimal stem cells in 100 ml of physiological saline. The MMSCs were injected less than 48 hours after the retrobulbar injection of neural progenitor cells.

Example 7

Diagnostic Methods

The following diagnostic methods were used to evaluate treatment efficacy:

1. Computerized Perimetry Using Humphrey® Field Analyzer

Computerized perimetry using Humphrey® Field Analyzer (Carl Zeiss Meditec AG) ElectroRetinoGram (ERG) was used to measure the eye's electrical response to light. The response consists of a negative-going a-wave, followed by a positive-going b-wave. The leading edge of the a-wave provided a direct measure of photoreceptor activity, while the b-wave provided a reflection of the action of cells in the bipolar cell region.

2. Electro-Oculography (EOG)

The function of the pigment epithelium was assessed by measuring "dark trough," "light peak," and the Arden ratio during ElectroOculoGraphy (EOG).

3. Stratus OCT Analysis

Imaging of retinal nerve fiber layer, optic nerve head and macular was performed by using Stratus OCT apparatus (Carl Zeiss Meditec AG) that incorporates optical coherence tomography technology.

4. Fluorescein Angiography

The circulation of the retina was examined by using fluorescein angiography technique.

5. Doppler Sonography

The anatomy of orbital arteries and veins was examined by Doppler sonography. The function of the coagulation system was evaluated by standard tests.

6. Immunoassay

Blood samples were collected, aliquotted and frozen for later determination of Brain-Derived Neurotrophic Factor (BDNF). BDNF serum levels will be determined by ELISA technique.

Blood vessel index is measured by using imaging software developed by Fedorov's Eye. Center—the higher number, the worse blood vessel conditions.

Results

Patients

Seven patients with diabetes were enrolled in the study. The patients had varying degrees of diabetic retinopathy and diabetic optic neuropathy. The patients were observed at baseline and at day 2, day 8, day 14, day 30, day 60, day 90 after treatment.

Stem Cell Treatment

Patients received one retrobulbar injection of 7,000,000 neural progenitor cells in each eye and one intravenous injection of 100,000,000 mesenchymal stem cells. The MMSCc were injected less than 48 hours after the retrobulbar injection of neural progenitor cells.

Methods

Computerized perimetry was performed by using Humphrey® Field Analyzer (Carl. Zeiss Meditec AG). ElectroRetinoGram (ERG) was used to measure the eye's electrical response to light. The response consists of a negative-going awave, followed by a positive-going b-wave. The leading edge of the a-wave provided a direct measure of photoreceptor activity, while the b-wave provided a reflection of the action of cells in the bipolar cell region http://en.wikipedia.org/wiki/Electroretinogram The function of the pigment epithelium was assessed by measuring "dark trough", "light peak", and the Arden ratio during ElectroOculoGraphy (EOG) http://en.wikipedia.org/wiki/Electrooculography Imaging of retinal nerve fiber layer, optic nerve head and macular was performed by using Stratus OCT apparatus (Carl Zeiss Meditec AG) that incorporates optical coherence tomography technology. http://www.lightlabimaging.com/oct.html The circulation of the retina was examined by using fluorescein angiography technique http://en.wikipedia.org/wiki/Fluorescein_angiography The anatomy of orbital arteries and veins was examined by Doppler sonography. The function of the coagulation system was evaluated by standard tests. Blood samples are currently collected, aliquotted and frozen for later determination of Brain-Derived Neurotrophic Factor (BDNF). BDNF serum levels will be determined by ELISA technique. http://en.wikipedia.org/wiki/BDNF Patient 1

Identification Number: 975739

Diagnosis: type II diabetes, diabetic angiopathy

Visual acuity: 1.0 OU (corresponds to USA 20/20 in each eye".)

http://en.wikipedia.org/wiki/Visual_acuity

Treatment:

Patient #1 received mesenchymal stem cells.

Fundus photographs confirmed diagnosis of angiopathy (total integrated score was 0.10). Fluorescein angiography showed signs of dystrophic chorio-retinal lesions in the central retina.

Doppler sonography revealed decreased blood flow speed in left supraorbital artery and left central retinal artery. ElectroRetinoGram demonstrated a- and b-waves of reduced amplitudes in response to red light, as well as b-waves of increased amplitudes in response to white light (in both eyes). This suggests retinal hypoxia and ischemia that was more pronounced in macular area. Ischemia was accompanied by a compensatory increase in rod synaptic signaling to the inner retina (b-wave). The Arden ratio (light peak/dark trough amplitude) was decreased in the right eye, which indicated retinal pigment epithelial abnormalities.

Computerized perimetry revealed a small numbers of blind spots (absolute and relative scotomas) in both eyes that further confirmed diagnosis of retinal ischemia.

Two days after i.v. injection of mesenchymal stem cells, the symptoms of retinal ischemia exacerbated slightly (insignificantly). Tests included ElectroRetinoGram and computerized perimetry (Arden coefficient has gone up; red light induced and b-waves have gone down; white light induced b-wave gone down). Stem cell injection caused "hemodynamic changes" on day 2. Decreased blood flow caused swelling. Swelling induced hypoxic conditions in the retina.

On day 6 post-treatment, Patient #1 showed signs of improvement in edema and ischemia. That conclusion was made based on the following: (1) Arden ratio had decreased. The ratio dropped 2-fold in the right eye compared to the value detected on day 2 post-treatment. (2) red light induced a-wave increased 2-fold in the right eye and 3.5-fold in the left eye. (3) red light induced b-wave increased 1.3-fold in the right eye and 1.5-fold in the left eye. (4) white light induced bwave amplitude decreased to normal values in both eyes.

On day 30 post-treatment, Patient #1 showed signs of improved blood flow through retinal veins. That conclusion was made by analysing vessel morphology from ocular fundus images.

Red light induced a-wave: amplitudes and Arden ratios were slightly above normal range. White light induced b-wave amplitudes were within upper-normal range, which may suggest improved blood flow.

Computerized perimetry of the left eye revealed improved fovea sensitivity. No blind spots were detected in the left eye. Perimetry of the right eye showed lower number of blind spots compared to pretreatment level (1 absolute and 4 relative scotomas).

On day 60 post-treatment, Patient #1 showed normal Arden ratio values in the left eye, which suggests improved blood supply to pigment epithelium. Test results remained did not change between day 60 and day 90.

Tests performed 6 and 9 months after stem cell injection demonstrated the following: (1) blind spots had disappeared completely in both eyes; (2) Total integrated score had improved from 9 to 4.7 (the score reflects the retinal vascular tree morphology).

Patient 2

Identification Number: 663391

Diagnosis: type I diabetes, diabetic angiopathy, diabetic optic neuropathy.

Visual acuity: 1.0 OU (corresponds to USA 20/20 in each eye")

Fundus photographs and fluorescein angiography confirmed diagnosis of diabetic angiopathy in its sub-clinical stage. Total integrated score was 9. The score reflects morphology of the retinal vascular tree (length, diameter, vascular loops and coils).

Doppler sonography results—Left eye: blood flow speed was at the upper normal range. Right eye: blood flow speed was 2 times greater than normal in right supraorbital artery and right central retinal artery. ElectroRetinoGrams showed b-waves of reduced amplitudes in response to red and white light stimulation in both eyes. That indicated decreased function of retinal bipolar cells and Muhller cell because of ischemic/hypoxic condition. Arden ratio was found to be in the upper normal range in the left eye, which suggested compensatory response of pigment epithelial cells to ischemia.

Computerized perimetry did not show any blind spots. Optical coherence tomography showed slight thinning of 4 out of 12 fibers of optic nerve in the upper nasal area in the left eye.

Patient #2 received one retrobulbar injection of 7,000,000 neural progenitor cells in each eye, and one intravenous injection of 100,000,000 mesenchymal stem cells.

Day 2 post-treatment. Blood flow speed in the left eye arteries had decreased to normal values. Arden ratio moved from elevated to the lower normal range. Amplitudes of b-waves increased slightly in both eyes in response to red light stimulation. Computerized perimetry registered increased sensitivity of the fovea.

Day 7 post-treatment. Amplitudes of b-waves increased slightly in the right eye in response to white light stimulation. All other tested parameters did not change compared to day 2 values.

Day 14 and day 30 post-treatment. No changes compared to day 2 findings.

Day 60 post-treatment. No changes compared to day 2 findings. Optical coherence tomography showed slight increase in diameter of optic nerve fibers in both eyes. Analysis of vessel morphology from ocular fundus images showed sighs of improved blood flow through retinal veins.

Optical coherence tomography tests performed 3 and 4 months after stem cell injection demonstrated that optic nerve fibers in the left eye increased in diameter. Optic nerve fiber morphology remained stable by 6 month post-treatment. The achieved results persisted at month 9 post-treatment.

Patient 3
Identification Number: 633808
Diagnosis: Type I diabetes.
Right eye: proliferative retinopathy, swelling of the macula was treated by laser surgery (pan-retinal photocoagulation). Left eye: proliferative retinopathy, swelling of the macula, no laser surgery. Optic neuropathy.
Right eye opthalmoscopy: optic nerve disk is pale light red in color; newly formed blood vessels were detected in the area between nerve disk and macula; fewer bleeding spots as well as defects caused by laser coagulation were detected.

Left eye opthalmoscopy: optic nerve disk is pale light red in color; newly formed blood vessels leaked fluid and lipids onto the macula.

Fundus photographs showed significant deterioration of morphology of the retinal vascular tree (total integrated score was 24).

Doppler sonography demonstrated slight decrease in blood flow speed in orbital arteries.

ElectroRetinoGrams showed significant decrease in electric activity of bipolar retinal cells and Muhller cells in the central and peripheral areas. Pigment epithelium response to light was lower in the right eye.

Computerized perimetry showed a decreased sensitivity of the fovea that was more pronounced in the right eye. Absolute and relative blind spots were found in the left eye. No absolute scotomas were found in the right eye, although few relative blind spots were detected.

Optical coherence tomography showed significant thinning of optic nerve fibers in the upper temporal of the left eye: 6 segments out of 12 segments had average fiber diameter of 60 μm.

Patient #3 received one retrobulbar injection of 7,000,000 neural progenitor cells in the left eye, and intravenous injection of 100,000,000 mesenchymal stem cells. Only left eye was injected with stem cells. OS must be typed instead of OU. OS means Oculus Sinister (Left Eye). OU means Oculus Uturque (both eye).

Day 2 Post-Treatment
Arden ratio had increased. Left eye: a- and b-waves had gone up in amplitude in response to red and white light stimulation. Right eye: bwaves (white) increased; a-wave (red) increased. Computerized perimetry showed significant increase in sensitivity of the fovea in the right eye.

Day 7 Post-Treatment
Right eye: Pigment epithelium activity (Arden ratio) decreased below normal and b-waves (both red and white light induced) had gone up in amplitude compared to pre-treatment levels. Number of absolute blind spots decreased. Sensitivity of the fovea stayed at day 2 level. Left eye: Pigment epithelium activity (Arden ratio) decreased to pre-treatment levels a- and b-wave responses stayed at day 2 level. Doppler sonography demonstrated increase in blood flow speed that was more pronounced in the right eye.

Day 14 post-treatment. No changes were found compared to day 7.

Day 30 post-treatment. Arden ration decreased below pre-treatment values. Left eye. Optic nerve fibers increased in diameter from 60 μm to 72 μm. Fundus photographs showed a positive trend: total integrated score decreased from 24 to Right eye. No changes were found compared to day 14.

Day 60 post-treatment. Arden ration remained below normal. Left eye: a-waves and b-waves (white light) remained above pre-treatment values a-waves (red) remained above pre-treatment values. Right eye: a-waves and b-waves (white light) remained above pre-treatment values b-waves (red) remained at pre-treatment values. Sensitivity of the fovea remained at increased level.

Doppler sonography showed increased blood flow speed that was 2 times greater than pre-treatment values. Morphological picture of optic nerve fibers and retinal vessels continued to improve. Opthalmoscopy revealed no new bleeding spots; resorbtion of old hemorrhages was noticed.

Optical coherence tomography tests performed 3 and 4 months after stem cell injection showed a trend toward increase in diameter of optic nerve fibers in the left eye. Optic nerve fiber morphology remained stable by 6 month post treatment. Light sensitivity of the fovea remained stable. The achieved results persisted at 9 months post-treatment.

Patient 4
Identification Number: 433197
Diagnosis: Type I diabetes.
Right eye: pre-proliferative retinopathy, swelling of the macula with cyst formation. Right eye was treated by laser surgery (pan-retinal photocoagulation).
Left eye: pre-proliferative retinopathy, swelling of the macula.
Opthalmoscopy of both eyes: optic nerve disk is pale light red in color;
numerous bleeding spots; the damaged blood vessels leak fluid.

Total integrated score was 14. Linear blood flow speed (Doppler sonography) was decreased on the right and increased on the left. Right-to-Left ratio was 5. ElectroRetinoGrams of both eyes showed decrease in b-waves (white), decrease in a- and b-waves (red). Pigment epithelium response to light was decreased. Few blind spots were found. Optic nerve electric activity was slightly decreased.

Macular cyst was found in the right eye. Elevated fibrinogen levels and decreased thrombin time indicated the propensity to develop blood clots (hypercoaguability).

Patient #4 received one retrobulbar injection of 7,000,000 neural progenitor cells in the left eye, and intravenous injection of 100,000,000 mesenchymal stem cells. OS must be typed instead of OU. OS means Oculus Sinister (Left Eye). OU means Oculus Uturque (both eye).

Day 2 Post-Treatment

Arden ratio had increased in both eyes; the increase was more pronounced in the right eye. White light stimulation: a- and b-waves increased slightly in both eyes. Red light stimulation: a-waves increased significantly and reached normal values. Blind spots were not detected. Small decrease in blood flow speed was detected on the left eye.

Day 7 post-treatment. Blood flow speed decreased to normal values. Electric activity of pigment epithelium increased on the left and decreased on the right (there was no left/right asymmetry). Other tests did not show any changes compared to day 2.

Day 14 post-treatment. Blood flow speed stayed within normal range on the left. On the right, electric activity of pigment epithelium continued to decrease; blood flow speed increased slightly. Fibrinogen levels decreased.

Day 30 post-treatment. Arden ratios slightly decreased in both eyes compared to day 14, but the ratios still remained above day 0 levels. Right eye: a- and b-waves increased in amplitude 1.5-fold-2-fold. Relative blind spots re-appeared in the central area. Coherent tomography showed signs of progressing macular edema that might increase a risk of a cyst burst. Left eye. Red light stimulation revealed an increase in a- and b-waves amplitude.

Fundus photographs showed a positive trend (total integrated score decreased from 14 to 11). Opthalmoscopy revealed no fresh bleeding spots; resorbtion of old hemorrhages was noticed. Fibrinogen levels continued to drop, although remaining above normal values. At the moment, the patient is undergoing a course of laser coagulation treatment directed towards suppressing macula edema in the right eye.

4-6 months after stem cell injections, notwithstanding that laser coagulation treatment was carried out (which is often-accompanied by a decrease in retinal function) Arden ratios remained significantly above the pre-treatment levels in both eyes. In spite of the fact that amplitude of a- and b-waves continued to decrease in both eyes, nevertheless it has never fallen down below the pre-treatment levels.

Patient 5

Identification Number 653212

Diagnosis. Type I diabetes; pre-proliferative retinopathy in both eyes.

Opthalmoscopy revealed numerous bleeding spots in both eyes; blood vessels were swollen and leaked fluid. Doppler sonography revealed a profound decrease in blood flow speed in both eyes. Amplitude of a- and b-waves induced by red and white light were reduced compared to normal values. Electric activity of pigment epithelium was depressed significantly in both eyes. Computerized perimetry detected several blind spots. Test for optic nerve excitability revealed significantly reduced values in both eyes. Thickness measurements performed by optical coherence tomography demonstrated that edema affected both the macula and retinal nerve fiber layer in the left eye. (http://www.iovs.org/cgi/content/full/46/10/3807) Fibrinogen levels was found to be at the upper normal limit, thrombin time was decreased. Patient #5 received one retrobulbar injection of 7,000,000 neural progenitor cells in each eye, and one intravenous injection of 100,000,000 mesenchymal stem cells.

Day 2 post-treatment. Optic nerve excitability had increased.

Day 8 and day 14 post-treatment. Optic nerve excitability remained at the level detected on day 2.

Day 30 post-treatment. Arden ratios increased. Amplitudes of b-waves (red and white) increased in both eyes.

Day 60 post-treatment. Thickness measurements performed by optical coherence tomography demonstrated that edema that affected the macula and retinal nerve fiber layer had decreased. Arden ratios continued to increase in both eyes (the increase was more evident on the left). Amplitudes of b-waves (red and white) continued to; increase in both eyes.

After 3-4 months, thickness measurements showed that edema that affected the macula and retinal nerve fiber layer did not increase compared to day 60.

Patient 6 identification number: 461814 date of birth: 1947

Diagnosis. Type I diabetes; proliferative retinopathy in both eyes. In 1995, the patient had undergone vitrectomy and panretinal photocoagulation on both eyes (http://en.wikipedia.org/wiki/Vitrectomy). Inspection with opthalmoscope did not produce clear images of the retina. The eye's electrical response to light was greatly reduced in all measured parameters (a- and b-waves, Arden ratios, etc.). Optic coherent tomography detected atrophy of retinal nerve fiber layer. B-scan ultrasonography of the retina and vitreous. (http://www.emedicine.com/oph/topic757.htm) Left eye: No vitreous separation was found.

Attachment of the retina to posterior hyaloid membrane observed.

Right eye: No vitreous separation was found. Attachment of the retina to posterior hyaloid membrane observed Vitreous body was cloudy.

Patient #6 received one retrobulbar injection of 7,000,000 neural progenitor cells in each eye, and one intravenous injection of 100,000,000 mesenchymal stem cells.

Day 14 and 30 post-treatment. Arden ratios increased in both eyes. Amplitudes of a- and b-waves (red and white light) increased in both eyes. Optic nerve excitability had improved.

After 2 and 3 months post-treatment, the eye's electrical response to light continued to improve. Electric response threshold of inner retinal layers had decreased toward normal values: 25% below pretreatment level in the right eye; 50% below pretreatment level in the left eye. Thickness of retinal nerve fiber layer increased significantly.

Four months post-treatment, studies on the field of vision demonstrated significant expansion of the borders of the field of vision in both eyes.

Six months post-treatment, electrophysiologic studies and optic coherent tomography confirmed that the achieved results were persistent. Further expansion of the borders of the field of vision in both eyes was observed.

Patient 7

Identification number 796382

Diagnosis: type I diabetes. Diabetic retinopathy in both eyes. Pseudophakia in the left eye (http://en.wikipedia.org/wiki/Pseudophakia). Inspection with opthalmoscope did not produce clear images of the interior surface of the eye. The eye's electrical response to light was greatly reduced in all measured parameters (a- and b-waves, Arden ratios, etc.). Optic coherent tomography detected edema that affected retinal nerve fiber layer.

Patient #7 received one retrobulbar injection of 7,000,000 neural progenitor cells in each eye, and one intravenous injection of 100,000,000 mesenchymal stem cells.

Day 14 and 30 post-treatment. Significant improvement in the left eye (Arden ratio increased by 15%). Amplitudes of a-waves (red and white light) increased. Optic nerve excitability improved slightly. Electric response threshold of inner retinal layers had decreased by 30% in both eyes.

After 2 and 3 months post-treatment, the eye's electrical response to light continued to improve (left eye tests were stable, right eye tests continued to improve). Electric response threshold of inner retinal layers had decreased toward upper-normal values in both eyes. Edema that affected retinal nerve fiber layer diminished. Six months post-treatment, as judged from the electrophysiological data the achieved results persisted. This testifies not only to the presence of a positive trend as concerns retina and optical nerve.
Patient 8
Identification number: 1001651
date of birth: 1947
Diagnosis. Type II diabetes; diabetic angiopathy.
Visual acuity: 1.0 OU (corresponds to USA 20/20 in each eye")
While studying the amplitude characteristics of the initial ERG (ElectroRetinoGram) an insignificant reduction in the parameters of ERG, EOG (ElectroOculoGraphy) and electric lability was observed. During computerized perimetry studies (120 points) an insignificant reduction in foveal sensitivity in the fields of vision of both eyes was observed. Solitary absolute and relative scotomas were detected—ischemic injury.

The patient was treated by i.v. injection of MMSCs ($10^8$ cells) and retrobulbar injection of NPCs ($7 \times 10^6$ cells) in each eye.

Two weeks post-treatment no significant changes were observed. In one month post-treatment increase in the electric lability of the optic nerve was revealed. In two months post-treatment the parameters of the electric lability of the optic nerve correspond to normal levels; ERG data testify to the normalization of the parameters; computerized perimetry data (test on 120 points) testify to the increase in the foveal sensitivity parameters to normal levels; reduction in the number of scotomas.

CONCLUSIONS

The results of treating patients 1-8 are illustrated in FIGS. 21-24 and 26-42. Based on the results, the following general conclusions are made:

Treating diabetic retinopathy by administering ectodermal cells to the retinal tissue and intravenously administering mesenchymal cells resulted in a positive tendency toward normalization of functional activity of the upper retinal layer, the optic nerve and the pigment epithelium presumably because of improvement of hemodynamics of blood flow in eye vessels.

The most noticeable Patient-Specific Findings (specific positive responses of patients) after the treatment: were as follows:

Patient 1: One month after mesenchymal stem cells injection, Patient #1 showed a positive trend toward improved functional status. Outer retinal layers and pigment epithelium demonstrated a trend toward normalization that could be explained by improved blood supply. The number or relative and absolute scotomas was significantly reduced.

Patient 2: Patient #2 demonstrated a positive trend toward improved functional status. Outer retinal layers, pigment epithelium and optic nerve fibers demonstrated a trend toward normalization that could be explained by improved blood supply. Thickness of the optic nerve fiber layer increased and became close to normal values.

Patient 3: Patient #3 showed a "positive trend" toward improved functional status. Outer retinal layers, pigment epithelium and optic nerve fibers demonstrated a trend toward normalization that could be explained by improved blood supply. There were improvements of blood flow in eye blood vessels, positive dynamics of resorption of hemorrhages, no new micro bleedings.

Patient 4: One month after treatment, Patient #4 showed "a positive trend" toward improved functional status in the left eye. Pigment epithelium exhibited positive dynamics. NB: Macular edema was progressing in the right eye. The edema "was approriately treated" using laser coagulation treatment. There was resorption of initially numerous hemorrhages, no new micro bleedings.

Patient 5: Edema of nerve fiber layer and macular edema decreased. Pigment epithelium in both eyes exhibited a positive trend.

Patient 6: Significant improvement in the function of different layers of retina and optical nerve. Increase in the thickness of the nerve fiber layer and significant expansion of the borders of the field of vision.

Patient 7: Significant improvement in the function of different layers of retina and optical nerve. Decrease of edema of nerve fiber layer.

Patient 8: Increase in the functional activity of optic nerve, sensitivity of fovea and reduction in the number of scotomas in the filed of vision.

We claim:

1. A method for treating diabetic retinopathy in a subject comprising:
   administering ectodermal cells to the retinal tissue of said subject; and
   intravenously administering mesenchymal cells to said subject;
   wherein said method treats said diabetic retinopathy.

2. The method of claim 1, wherein said ectodermal cells are obtained from one or a combination of fetal neural tissue, adult neural tissue, and embryonic tissue.

3. The method of claim 1, wherein said mesenchymal cells are obtained from postnatal tissue.

4. The method of claim 1, wherein said mesenchymal cells are obtained from bone marrow.

5. The method of claim 1, wherein said mesenchymal cells are obtained from umbilical cord blood, placenta or combinations thereof.

6. The method of claim 1, wherein said ectodermal cells are injected by one or more of the administration routes selected from retrobulbarly, intravitreously, and subchoroidally.

7. A method for treating diabetic retinopathy in a subject comprising:
   administering ectodermal cells to the eye of said subject; and
   intravenously administering mesenchymal cells to said subject;
   wherein said method treats said diabetic retinopathy.

8. The method of claim 7, wherein said ectodermal cells are administered to the retinal tissue of said eye.

9. The method of claim 7, wherein said ectodermal cells are obtained from one or a combination of fetal neural tissue, adult neural tissue, and embryonic tissue.

10. The method of claim 7, wherein said mesenchymal cells are obtained from bone marrow.

11. The method of claim 7, wherein said ectodermal cells are injected by one or more of the administration routes selected from retrobulbarly, intravitreously, and subchoroidally.

12. The method of claim 7, wherein said ectodermal cells and/or said mesenchymal cells are derived from a cloned cell population.

* * * * *